(12) United States Patent
Bachmann

(10) Patent No.: US 9,200,078 B2
(45) Date of Patent: Dec. 1, 2015

(54) ANTIBODIES AGAINST PROSTATE-SPECIFIC STEM CELL ANTIGEN AND USE THEREOF

(75) Inventor: Michael Bachmann, Kelkheim (DE)

(73) Assignee: GEMoaB Monoclonals GmbH, Dresden (DE)

( * ) Notice: Subject to any disclaimer, the term of this patent is extended or adjusted under 35 U.S.C. 154(b) by 198 days.

(21) Appl. No.: 14/129,933

(22) PCT Filed: Jun. 29, 2012

(86) PCT No.: PCT/EP2012/062716
§ 371 (c)(1),
(2), (4) Date: Dec. 28, 2013

(87) PCT Pub. No.: WO2013/001065
PCT Pub. Date: Jan. 3, 2013

(65) Prior Publication Data
US 2014/0134155 A1     May 15, 2014

(30) Foreign Application Priority Data

Jun. 30, 2011   (DE) .................. 10 2011 118 022

(51) Int. Cl.
*C07K 16/30* (2006.01)
*A61K 39/395* (2006.01)
*C07K 16/28* (2006.01)
*A61K 39/00* (2006.01)

(52) U.S. Cl.
CPC ....... *C07K 16/3069* (2013.01); *A61K 39/39558* (2013.01); *C07K 16/28* (2013.01); *C07K 16/2809* (2013.01); *C07K 16/30* (2013.01); *A61K 2039/505* (2013.01); *C07K 2317/31* (2013.01); *C07K 2317/622* (2013.01); *C07K 2317/92* (2013.01)

(58) Field of Classification Search
CPC ... C07K 16/28; C07K 16/30; A61K 39/39558
USPC ........... 530/387.3, 387.7, 388.22; 435/320.1, 435/325, 69.1; 536/23.5
See application file for complete search history.

(56) References Cited

U.S. PATENT DOCUMENTS

2011/0142811 A1   6/2011   Ungerechts et al.

FOREIGN PATENT DOCUMENTS

| WO | 01/05427 A1 | 1/2001 |
|---|---|---|
| WO | 01/40309 A2 | 6/2001 |
| WO | 2009/032949 A2 | 3/2009 |

OTHER PUBLICATIONS

Feldmann A et al.: Retargeting of T cells to prostate stem cell antigenic expressing tumor cells: comparison of different anti-body formats; The Prostate 71:998-1011 (2011)—published online Dec. 28, 2010; see international search report.
Gu Z et al.: Anti-prostate stem cell antigen monoclonal antibody 1G8 induces cell death in vitro and inhibits tumor growth in vivo via a Fc independent mechanism. Cancer Res. 2005;65;9495-9500.
Morgenroth A et al.: Targeting of tumor cells expressing the prostate stem cell antigenic (PSCA) using genetically engineered T-cells; The Prostate 67:1121-1131 (2007).
Reiter R E et al.: Prostate stem cell antigen: A cell surface marker overexpressed in prostate cancer. Proc Natl Acad Sci USA, vol. 95, pp. 1735-1440, Feb. 1998.
Roehl K A et al.: Cancer progression and survival rates following anatomical radical retropubic prostatectomy in 3,478 consecutive patients: long-term results; The Journal of Urology; vol. 172, 910-914, Sep. 2004.
Thomas-Kaskel A K et al.: Vaccination of advanced prostate cancer patients with PSCA and PSA peptide-loaded dendritic cells induces DTH responses that correlate with superior overall survival. Int. J. Cancer, 119, 2428-2434 (2006).
Lepin E J et al.: An affinity matured minibody for PET imaging of prostate stem cell antigen (PSCA)-expressing tumors; Eur J Nucl Med Mol Imaging (2010) 37:1529-1538; see international search report.
Feldmann A et al.: Novel humanized and highly efficient bispecific antibodies mediate killing of prostate stem cell antigen-expressing tumor cells by CD8* and CD4* T cells; The Journal of Immunology; 2012; 189; 3249-3259—prepublished online Aug. 8, 2012; see international search report.
Morgenroth A: Herstellung chimärer Rezeptoren zur tumospezifischen Armierung polyklonaler, zytotoxischer T-Lymphozyten; dissertation; Technische Universität Dresden; Dec. 7, 2005; p. 53; see international search report.
Schwarzer A: Herstellung und Charakterisierung rekombinanter Antikörper für eine adjuvante Immuntherapie PSCA-positiver Tumore; Dissertation; Technische Universität Dresden; Jan. 1, 2006; see international search report.

*Primary Examiner* — Stephen Rawlings
(74) *Attorney, Agent, or Firm* — Gudrun E. Huckett

(57) ABSTRACT

The invention relates to recombinant antibodies which bind to prostate-specific stem cell antigen (PSCA). The antibody of the invention comprises complementarity-determining regions (CDR) having the following amino acid sequences: CDR of the variable region of the light chain: CDR1 SEQ ID No. 1, CDR2 SEQ ID No. 2, CDR3 SEQ ID No. 3, and CDR of the variable region of the heavy chain: CDR1 SEQ ID No. 4, CDR2 SEQ ID No. 5, CDR3 SEQ ID No. 6. The invention also embraces the use of the antibodies of the invention as medicinal products, especially for the treatment of tumor diseases, or as a diagnostic agent. The antibodies are suitable for use in the areas of medicine, pharmacy and biomedical research.

19 Claims, 4 Drawing Sheets

Fig. 1

SEQUENCE LISTING

<160> NUMBER OF SEQ ID NOS: 172

<210> SEQ ID NO 1
<211> LENGTH: 11
<212> TYPE: PRT
<213> ORGANISM: Mus musculus

<400> SEQUENCE: 1

Gly Thr Ser Gln Asp Ile Asn Asn Tyr Leu Asn
1               5                   10

<210> SEQ ID NO 2
<211> LENGTH: 7
<212> TYPE: PRT
<213> ORGANISM: Mus musculus

```
<400> SEQUENCE: 2

Tyr Thr Ser Arg Leu His Ser
1               5

<210> SEQ ID NO 3
<211> LENGTH: 9
<212> TYPE: PRT
<213> ORGANISM: Mus musculus

<400> SEQUENCE: 3

Gln Gln Ser Lys Thr Leu Pro Trp Thr
1               5

<210> SEQ ID NO 4
<211> LENGTH: 5
<212> TYPE: PRT
<213> ORGANISM: Mus musculus

<400> SEQUENCE: 4

Ser Tyr Ser Met Ser
1               5

<210> SEQ ID NO 5
<211> LENGTH: 17
<212> TYPE: PRT
<213> ORGANISM: Mus musculus

<400> SEQUENCE: 5

Tyr Ile Asn Asp Ser Gly Gly Ser Thr Phe Tyr Pro Asp Thr Val Lys
1               5                   10                  15

Gly

<210> SEQ ID NO 6
<211> LENGTH: 13
<212> TYPE: PRT
<213> ORGANISM: Mus musculus

<400> SEQUENCE: 6

Arg Met Tyr Tyr Gly Asn Ser His Trp His Phe Asp Val
1               5                   10

<210> SEQ ID NO 7
<211> LENGTH: 33
<212> TYPE: DNA
<213> ORGANISM: Mus musculus

<400> SEQUENCE: 7
gggacaagtc aggacattaa caattattta aac                              33

<210> SEQ ID NO 8
<211> LENGTH: 33
<212> TYPE: DNA
<213> ORGANISM: Homo sapiens

<400> SEQUENCE: 8
ggtacatccc aagacatcaa taattatctc aac                              33

<210> SEQ ID NO 9
<211> LENGTH: 21
<212> TYPE: DNA
<213> ORGANISM: Mus musculus

<400> SEQUENCE: 9
```
tacacatcaa gattacactc g                                              21

<210> SEQ ID NO 10
<211> LENGTH: 21
<212> TYPE: DNA
<213> ORGANISM: Homo sapiens

<400> SEQUENCE: 10
tacacatcca ggctgcattc c                                              21

<210> SEQ ID NO 11
<211> LENGTH: 27
<212> TYPE: DNA
<213> ORGANISM: Mus musculus

<400> SEQUENCE: 11
caacagtcta agacgcttcc gtggacg                                        27

<210> SEQ ID NO 12
<211> LENGTH: 27
<212> TYPE: DNA
<213> ORGANISM: Homo sapiens

<400> SEQUENCE: 12
cagcagtcaa agacattacc atggaca                                        27

<210> SEQ ID NO 13
<211> LENGTH: 15
<212> TYPE: DNA
<213> ORGANISM: Mus musculus

<400> SEQUENCE: 13
tcctattcca tgtct                                                     15

<210> SEQ ID NO 14
<211> LENGTH: 15
<212> TYPE: DNA
<213> ORGANISM: Homo sapiens

<400> SEQUENCE: 14
agttactcta tgtca                                                     15

<210> SEQ ID NO 15
<211> LENGTH: 51
<212> TYPE: DNA
<213> ORGANISM: Mus musculus

<400> SEQUENCE: 15
tacattaatg atagtggtgg tagcaccttt tatccagaca ctgtgaaggg c              51

<210> SEQ ID NO 16
<211> LENGTH: 51
<212> TYPE: DNA
<213> ORGANISM: Homo sapiens

<400> SEQUENCE: 16
tacattaatg attcaggtgg aagtacattc tatccggaca cggttaaagg t              51

<210> SEQ ID NO 17
<211> LENGTH: 39
<212> TYPE: DNA
<213> ORGANISM: Mus musculus

<400> SEQUENCE: 17

```
cggatgtact acggtaatag ccactggcac ttcgatgtc                                   39
```

<210> SEQ ID NO 18
<211> LENGTH: 39
<212> TYPE: DNA
<213> ORGANISM: Homo sapiens

<400> SEQUENCE: 18

```
cgtatgtatt atggcaatag tcactggcac tttgacgtc                                   39
```

<210> SEQ ID NO 19
<211> LENGTH: 348
<212> TYPE: DNA
<213> ORGANISM: Mus musculus

<400> SEQUENCE: 19

```
gatattgtga tgacacagtc tacatcctcc ctgtctgcct ctctgggaga cagagtcacc           60
atcaattgcg ggacaagtca ggacattaac aattatttaa actggtatca gcagaaacca          120
gatggaagtg ttaaactcct gatctactac acatcaagat tacactcggg agtcccatcc          180
aggttcagtg gcagtgggtc tggaacagat tattctctca ccattagcaa cctggagcaa          240
ggggatattg ccacttactt ctgccaacag tctaagacgc ttccgtggac gttcggtgga          300
ggcaccaagc tggaactcaa acgggctgat gctgcaccaa ctgtatcc                       348
```

<210> SEQ ID NO 20
<211> LENGTH: 116
<212> TYPE: PRT
<213> ORGANISM: Mus musculus

<400> SEQUENCE: 20

```
Asp Ile Val Met Thr Gln Ser Thr Ser Ser Leu Ser Ala Ser Leu Gly
1               5                   10                  15

Asp Arg Val Thr Ile Asn Cys Gly Thr Ser Gln Asp Ile Asn Asn Tyr
            20                  25                  30

Leu Asn Trp Tyr Gln Gln Lys Pro Asp Gly Ser Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Gly Asp Ile Ala Thr Tyr Phe Cys Gln Gln Ser Lys Thr Leu Pro Trp
                85                  90                  95

Thr Phe Gly Gly Gly Thr Lys Leu Glu Leu Lys Arg Ala Asp Ala Ala
            100                 105                 110

Pro Thr Val Ser
        115
```

<210> SEQ ID NO 21
<211> LENGTH: 363
<212> TYPE: DNA
<213> ORGANISM: Mus musculus

<400> SEQUENCE: 21

```
gtacagctgc aggagtcagg gggagttttta gtgcagcctg agggtccct gaaactctcc           60
tgtgcagcct ctggattcac tttcagttcc tattccatgt cttggattcg ccagactcca          120
gacaggaggc tggagtgggt cgcatacatt aatgatagtg gtggtagcac cttttatcca          180
```

```
gacactgtga agggccgatt ctccatctcc agagacaatg ccaagaacac cctgtacctc    240
caaataagca gactgaggtc tggggacacg gccatttatt actgttcaag acggatgtac    300
tacggtaata gccactggca cttcgatgtc tggggcgcag ggaccacggt caccgtctcc    360
tca                                                                  363
```

<210> SEQ ID NO 22
<211> LENGTH: 121
<212> TYPE: PRT
<213> ORGANISM: Mus musculus

<400> SEQUENCE: 22

Val Gln Leu Gln Glu Ser Gly Gly Val Leu Val Gln Pro Gly Gly Ser
1               5                   10                  15

Leu Lys Leu Ser Cys Ala Ala Ser Gly Phe Thr Phe Ser Ser Tyr Ser
            20                  25                  30

Met Ser Trp Ile Arg Gln Thr Pro Asp Arg Arg Leu Glu Trp Val Ala
        35                  40                  45

Tyr Ile Asn Asp Ser Gly Gly Ser Thr Phe Tyr Pro Asp Thr Val Lys
    50                  55                  60

Gly Arg Phe Ser Ile Ser Arg Asp Asn Ala Lys Asn Thr Leu Tyr Leu
65                  70                  75                  80

Gln Ile Ser Arg Leu Arg Ser Gly Asp Thr Ala Ile Tyr Tyr Cys Ser
                85                  90                  95

Arg Arg Met Tyr Tyr Gly Asn Ser His Trp His Phe Asp Val Trp Gly
            100                 105                 110

Ala Gly Thr Thr Val Thr Val Ser Ser
        115                 120

<210> SEQ ID NO 23
<211> LENGTH: 321
<212> TYPE: DNA
<213> ORGANISM: Homo sapiens

<400> SEQUENCE: 23

```
gatatccaga tgactcaaag tcctagttcc ctgtctgcat cagtgggaga ccgggtgacc    60
attacatgcg gtacatccca agacatcaat aattatctca actggtatca gcagaagcca    120
ggcaaagttc ctaagttatt aatctactac acatccaggc tgcattccgg ggtgccctcc    180
cgcttttcgg gctccgggtc gggaaccgac tttaccctaa ccatatcttc cctgcagcct    240
gaagacgttg caacgtacta ttgtcagcag tcaaagacat accatggac atttggtggt    300 gggacgcaac tcactgtact t                                              321
```

<210> SEQ ID NO 24
<211> LENGTH: 107
<212> TYPE: PRT
<213> ORGANISM: Homo sapiens

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Gly Thr Ser Gln Asp Ile Asn Asn Tyr
            20                  25                  30

Leu Asn Trp Tyr Gln Gln Lys Pro Gly Lys Val Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Ser Lys Thr Leu Pro Trp
                85                  90                  95

Thr Phe Gly Gly Gly Thr Gln Leu Thr Val Leu
            100                 105

<210> SEQ ID NO 25
<211> LENGTH: 366
<212> TYPE: DNA
<213> ORGANISM: Homo sapiens

<400> SEQUENCE: 25
caggtgcagc tagtggagtc cggtggcggc ctcgttaagc cgggcggatc gctgcgcctt      60
tcatgtgccg catcaggatt cacattctcc agttactcta tgtcatggat tcggcaggca     120
cctggcaagg gattggaatg ggtctcgtac attaatgatt caggtggaag tacattctat     180
ccggacacgg ttaaaggtag atttaccatc agccgtgata acgcgaagaa tagcttgtac     240
ttacagatga atagcctgcg tgcagaggat actgctgtat attattgcgc tcgacgtatg     300
tattatggca atagtcactg gcactttgac gtctggggcc agggcacgac agttactgtc     360
tcttcg                                                                366

<210> SEQ ID NO 26
<211> LENGTH: 122
<212> TYPE: PRT
<213> ORGANISM: Homo sapiens

<400> SEQUENCE: 26

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Ser Trp Ile Arg Gln Ala Pro Gly Lys Gly Leu Glu Trp Val
        35                  40                  45

Ser Tyr Ile Asn Asp Ser Gly Gly Ser Thr Phe Tyr Pro Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Met Tyr Tyr Gly Asn Ser His Trp His Phe Asp Val Trp
            100                 105                 110

Gly Gln Gly Thr Thr Val Thr Val Ser Ser
        115                 120

<210> SEQ ID NO 27
<211> LENGTH: 11
<212> TYPE: PRT
<213> ORGANISM: Mus musculus

<400> SEQUENCE: 27

Arg Thr Ser Gln Asp Ile Ser Asn Tyr Leu Asn
1               5                   10

<210> SEQ ID NO 28
<211> LENGTH: 7
<212> TYPE: PRT

```
<213> ORGANISM: Mus musculus

<400> SEQUENCE: 28

Tyr Thr Leu Lys Leu Asn Ser
1               5

<210> SEQ ID NO 29
<211> LENGTH: 9
<212> TYPE: PRT
<213> ORGANISM: Mus musculus

<400> SEQUENCE: 29

Gln Gln Ser Lys Thr Leu Pro Trp Thr
1               5

<210> SEQ ID NO 30
<211> LENGTH: 5
<212> TYPE: PRT
<213> ORGANISM: Mus musculus

<400> SEQUENCE: 30

Ser Tyr Thr Met Ser
1               5

<210> SEQ ID NO 31
<211> LENGTH: 17
<212> TYPE: PRT
<213> ORGANISM: Mus musculus

<400> SEQUENCE: 31

Tyr Ile His Asn Gly Gly Gly His Thr Tyr Tyr Pro Asp Thr Ile Lys
1               5                   10                  15

Gly

<210> SEQ ID NO 32
<211> LENGTH: 13
<212> TYPE: PRT
<213> ORGANISM: Mus musculus

<400> SEQUENCE: 32

Arg Met Tyr Tyr Gly Asn Ser His Trp Tyr Phe Asp Val
1               5                   10

<210> SEQ ID NO 33
<211> LENGTH: 33
<212> TYPE: DNA
<213> ORGANISM: Mus musculus

<400> SEQUENCE: 33
aggacaagcc aggacattag caactatttA aac                                   33

<210> SEQ ID NO 34
<211> LENGTH: 33
<212> TYPE: DNA
<213> ORGANISM: Homo sapiens

<400> SEQUENCE: 34
cggacctcac aagacatcag caactatctg aat                                   33

<210> SEQ ID NO 35
<211> LENGTH: 21
<212> TYPE: DNA
<213> ORGANISM: Mus musculus
```

```
<400> SEQUENCE: 35
tacacattaa aattaaattc a                                              21

<210> SEQ ID NO 36
<211> LENGTH: 21
<212> TYPE: DNA
<213> ORGANISM: Homo sapiens

<400> SEQUENCE: 36
tacacattaa aactaaattc c                                              21

<210> SEQ ID NO 37
<211> LENGTH: 27
<212> TYPE: DNA
<213> ORGANISM: Mus musculus

<400> SEQUENCE: 37
caacagagta aaacacttcc gtggacg                                        27

<210> SEQ ID NO 38
<211> LENGTH: 27
<212> TYPE: DNA
<213> ORGANISM: Homo sapiens

<400> SEQUENCE: 38
cagcagtcca aaccctgcc ttggacc                                         27

<210> SEQ ID NO 39
<211> LENGTH: 15
<212> TYPE: DNA
<213> ORGANISM: Mus musculus

<400> SEQUENCE: 39
tcctatacca tgtct                                                     15

<210> SEQ ID NO 40
<211> LENGTH: 15
<212> TYPE: DNA
<213> ORGANISM: Homo sapiens

<400> SEQUENCE: 40
agctatacaa tgtct                                                     15

<210> SEQ ID NO 41
<211> LENGTH: 51
<212> TYPE: DNA
<213> ORGANISM: Mus musculus

<400> SEQUENCE: 41
tacattcata atggtggtgg tcacacctac tatccagaca ccataaaggg c              51

<210> SEQ ID NO 42
<211> LENGTH: 51
<212> TYPE: DNA
<213> ORGANISM: Homo sapiens

<400> SEQUENCE: 42
tacatccata atggaggcgg tcacacctac tatcctgaca ctatcaaagg a              51

<210> SEQ ID NO 43
<211> LENGTH: 39
<212> TYPE: DNA
<213> ORGANISM: Mus musculus
```

<400> SEQUENCE: 43
cgaatgtact acggtaatag ccactggtac ttcgatgtc                         39

<210> SEQ ID NO 44
<211> LENGTH: 39
<212> TYPE: DNA
<213> ORGANISM: Homo sapiens

<400> SEQUENCE: 44
cgtatgtact acgggaacag ccactggtac ttcgacgtg                         39

<210> SEQ ID NO 45
<211> LENGTH: 348
<212> TYPE: DNA
<213> ORGANISM: Mus musculus

<400> SEQUENCE: 45
gatattgtga tgacacagtc tccatcctcc ctgtctgcct ctctgggcga cagagtcacc    60
atcaattgca ggacaagcca ggacattagc aactatttaa actggtatca gctgacacca   120
gatggaactg ttaaactcct gatctactac acattaaaat taaattcagg agtcccatca   180
aggttcagtg gcagtgggtc tgggacagat tattctctca ccattaacaa cctggagaaa   240
gaggattttg ccacttattt ttgccaacag agtaaaacac ttccgtggac gttcggtgga   300
ggcaccaagc tggaaatcaa gcgggctgat gctgcaccaa ctgtatcc              348

<210> SEQ ID NO 46
<211> LENGTH: 116
<212> TYPE: PRT
<213> ORGANISM: Mus musculus

<400> SEQUENCE: 46

Asp Ile Val Met Thr Gln Ser Pro Ser Ser Leu Ser Ala Ser Leu Gly
1               5                   10                  15
Asp Arg Val Thr Ile Asn Cys Arg Thr Ser Gln Asp Ile Ser Asn Tyr
                20                  25                  30
Leu Asn Trp Tyr Gln Leu Thr Pro Asp Gly Thr Val Lys Leu Leu Ile
            35                  40                  45
Tyr Tyr Thr Leu Lys Leu Asn Ser Gly Val Pro Ser Arg Phe Ser Gly
        50                  55                  60
Ser Gly Ser Gly Thr Asp Tyr Ser Leu Thr Ile Asn Asn Leu Glu Lys
65                  70                  75                  80
Glu Asp Phe Ala Thr Tyr Phe Cys Gln Gln Ser Lys Thr Leu Pro Trp
                85                  90                  95
Thr Phe Gly Gly Gly Thr Lys Leu Glu Ile Lys Arg Ala Asp Ala Ala
            100                 105                 110
Pro Thr Val Ser
        115

<210> SEQ ID NO 47
<211> LENGTH: 363
<212> TYPE: DNA
<213> ORGANISM: Mus musculus

<400> SEQUENCE: 47
caggtgaagc tgcaggagtc tggggggaggt ttagtgcagc ctggagggtc cctgaaactc    60
tcctgtgtag cctctggatt cactttcagt tcctatacca tgtcttgggt tcgccggact   120

```
ccagagaaga ggctggaatg ggtcgcatac attcataatg gtggtggtca cacctactat    180
ccagacacca taaagggccg attcaccatc tccagagaca atgccaagaa caccctgttc    240
ctggaaatga gcagtctgaa gtctgaagac acggccatgt attactgtac aagacgaatg    300
tactacggta atagccactg gtacttcgat gtctggggcg cagggaccct ggtcaccgtc    360
tcc                                                                  363
```

<210> SEQ ID NO 48
<211> LENGTH: 121
<212> TYPE: PRT
<213> ORGANISM: Mus musculus

<400> SEQUENCE: 48

```
Gln Val Lys Leu Gln Glu Ser Gly Gly Gly Leu Val Gln Pro Gly Gly
1               5                   10                  15

Ser Leu Lys Leu Ser Cys Val Ala Ser Gly Phe Thr Phe Ser Ser Tyr
            20                  25                  30

Thr Met Ser Trp Val Arg Arg Thr Pro Glu Lys Arg Leu Glu Trp Val
        35                  40                  45

Ala Tyr Ile His Asn Gly Gly Gly His Thr Tyr Tyr Pro Asp Thr Ile
    50                  55                  60

Lys Gly Arg Phe Thr Ile Ser Arg Asp Asn Ala Lys Asn Thr Leu Phe
65                  70                  75                  80

Leu Glu Met Ser Ser Leu Lys Ser Glu Asp Thr Ala Met Tyr Tyr Cys
                85                  90                  95

Thr Arg Arg Met Tyr Tyr Gly Asn Ser His Trp Tyr Phe Asp Val Trp
            100                 105                 110

Gly Ala Gly Thr Ser Val Thr Val Ser
        115                 120
```

<210> SEQ ID NO 49
<211> LENGTH: 321
<212> TYPE: DNA
<213> ORGANISM: Homo sapiens

<400> SEQUENCE: 49

```
gatatccaga tgacgcaatc accgagttct ctatccgcgt cggttggcga cagagtgact    60
atcacatgtc ggacctcaca agacatcagc aactatctga attggtatca acaaaagcca    120
ggcaaggctc ccaagctatt aatttattac acattaaaac taaattccgg tgtcccatcc    180
agattctcgg gtagcgggtc ggggacggat tttaccttca cgatatcctc cctccagcct    240
gaggacatcg ccacgtacta ctgccagcag tccaaaaccc tgccttggac cttcggtgga    300
gggaccaaag tcgaaattaa g                                              321
```

<210> SEQ ID NO 50
<211> LENGTH: 107
<212> TYPE: PRT
<213> ORGANISM: Homo sapiens

<400> SEQUENCE: 50

```
Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45
```

Tyr Tyr Thr Leu Lys Leu Asn Ser Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Ser Lys Thr Leu Pro Trp
                85                  90                  95

Thr Phe Gly Gly Gly Thr Lys Val Glu Ile Lys
                100                 105

<210> SEQ ID NO 51
<211> LENGTH: 366
<212> TYPE: DNA
<213> ORGANISM: Homo sapiens

<400> SEQUENCE: 51
gaggtacagc ttgttgaatc tggaggtggc ctggttcagc ccggcggctc actaaggctt      60
agttgtgccg cttcagggtt cacatttttcc agctatacaa tgtcttgggt ccgacaggca    120
ccgggaaaag gactggagtg ggtgagctac atccataatg gaggcggtca cacctactat    180
cctgacacta tcaaaggaag gttcactatc agtcgagata atgcgaagaa ctcactctac    240
ctacagatga acagcctgcg cgccgaagac accgctgtat actattgcgc acgccgtatg    300
tactacggga acagccactg gtacttcgac gtgtggggtc aaggtacgac cgttaccgtg    360
tcttcc                                                               366

<210> SEQ ID NO 52
<211> LENGTH: 122
<212> TYPE: PRT
<213> ORGANISM: Homo sapiens

<400> SEQUENCE: 52

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Thr Met Ser Trp Val Arg Gln Ala Pro Gly Lys Gly Leu Glu Trp Val
            35                  40                  45

Ser Tyr Ile His Asn Gly Gly Gly His Thr Tyr Tyr Pro Asp Thr Ile
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Met Tyr Tyr Gly Asn Ser His Trp Tyr Phe Asp Val Trp
                100                 105                 110

Gly Gln Gly Thr Thr Val Thr Val Ser Ser
            115                 120

<210> SEQ ID NO 53
<211> LENGTH: 318
<212> TYPE: DNA
<213> ORGANISM: Homo sapiens

<400> SEQUENCE: 53
gaaattgtgt tgacacagtc tccagccacc ctgtctttgt ctccagggga aagagccacc      60
ctctcctgca gtgccagttc aagtgtaagt tacatgcact ggtaccaaca gaaacctggc    120
caggctccca ggctcctcat ctatgacaca tccaaactgg cttctggcat cccagccagg    180

```
ttcagtggca gtgggtctgg gacagacttc actctcacca tcagcagcct agagcctgaa        240
gattttgcag tttattactg tcagcagtgg agtagtaacc cgctcacgtt cggcggaggg        300
accaaggtgg agatcaaa                                                      318
```

<210> SEQ ID NO 54
<211> LENGTH: 30
<212> TYPE: DNA
<213> ORGANISM: Homo sapiens

<400> SEQUENCE: 54

```
agtgccagtt caagtgtaag ttacatgcac                                          30
```

<210> SEQ ID NO 55
<211> LENGTH: 21
<212> TYPE: DNA
<213> ORGANISM: Homo sapiens

<400> SEQUENCE: 55

```
gacacatcca aactggcttc t                                                   21
```

<210> SEQ ID NO 56
<211> LENGTH: 27
<212> TYPE: DNA
<213> ORGANISM: Homo sapiens

<400> SEQUENCE: 56

```
cagcagtgga gtagtaaccc gctcacg                                             27
```

<210> SEQ ID NO 57
<211> LENGTH: 106
<212> TYPE: PRT
<213> ORGANISM: Homo sapiens

<400> SEQUENCE: 57

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Ser Tyr Met
            20                  25                  30

His Trp Tyr Gln Gln Lys Pro Gly Gln Ala Pro Arg Leu Leu Ile Tyr
        35                  40                  45

Asp Thr Ser Lys Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Trp Ser Ser Asn Pro Leu Thr
                85                  90                  95

Phe Gly Gly Gly Thr Lys Val Glu Ile Lys
            100                 105

<210> SEQ ID NO 58
<211> LENGTH: 10
<212> TYPE: PRT
<213> ORGANISM: Homo sapiens

<400> SEQUENCE: 58

Ser Ala Ser Ser Ser Val Ser Tyr Met His
1               5                   10

<210> SEQ ID NO 59

```
<211> LENGTH: 7
<212> TYPE: PRT
<213> ORGANISM: Homo sapiens

<400> SEQUENCE: 59

Asp Thr Ser Lys Leu Ala Ser
1               5

<210> SEQ ID NO 60
<211> LENGTH: 9
<212> TYPE: PRT
<213> ORGANISM: Homo sapiens

<400> SEQUENCE: 60

Gln Gln Trp Ser Ser Asn Pro Leu Thr
1               5

<210> SEQ ID NO 61
<211> LENGTH: 351
<212> TYPE: DNA
<213> ORGANISM: Homo sapiens

<400> SEQUENCE: 61
caggttcagc tggtgcagtc tggagctgag gtgaagaagc ctggggcctc agtgaaggtc     60
tcctgtaagg cttctggtta cacctttacc aaatatgtta tacattgggt gcgacaggcc    120
cctggacaag gcttgagtg gatgggatat attaatcctt acaatgatgt tagtaagtac     180
aatgagaagt tcagaggcag agtcaccatg accacagaca catccacgag cacagcctac    240
atggagctga ggagcctgag atctgacgac acggccgtgt attactgtgc gagaaataag    300
gattactatc ctatggacta ctggggccaa gggaccacgg tcaccgtctc g              351

<210> SEQ ID NO 62
<211> LENGTH: 15
<212> TYPE: DNA
<213> ORGANISM: Mus musculus

<400> SEQUENCE: 62
aaatatgtta tacat                                                      15

<210> SEQ ID NO 63
<211> LENGTH: 51
<212> TYPE: DNA
<213> ORGANISM: Mus musculus

<400> SEQUENCE: 63
tatattaatc cttacaatga tgttagtaag tacaatgaga agttcagagg c               51

<210> SEQ ID NO 64
<211> LENGTH: 27
<212> TYPE: DNA
<213> ORGANISM: Mus musculus

<400> SEQUENCE: 64
aataaggatt actatcctat ggactac                                         27

<210> SEQ ID NO 65
<211> LENGTH: 117
<212> TYPE: PRT
<213> ORGANISM: Homo sapiens

<400> SEQUENCE: 65

Gln Val Gln Leu Val Gln Ser Gly Ala Glu Val Lys Lys Pro Gly Ala
```

-continued

```
                1               5                   10                  15
        Ser Val Lys Val Ser Cys Lys Ala Ser Gly Tyr Thr Phe Thr Lys Tyr
                        20                  25                  30
        Val Ile His Trp Val Arg Gln Ala Pro Gly Gln Gly Leu Glu Trp Met
                        35                  40                  45
        Gly Tyr Ile Asn Pro Tyr Asn Asp Val Ser Lys Tyr Asn Glu Lys Phe
                    50                  55                  60
        Arg Gly Arg Val Thr Met Thr Thr Asp Thr Ser Thr Ser Thr Ala Tyr
        65                  70                  75                  80
        Met Glu Leu Arg Ser Leu Arg Ser Asp Asp Thr Ala Val Tyr Tyr Cys
                        85                  90                  95
        Ala Arg Asn Lys Asp Tyr Tyr Pro Met Asp Tyr Trp Gly Gln Gly Thr
                        100                 105                 110
        Thr Val Thr Val Ser
                115

<210> SEQ ID NO 66
<211> LENGTH: 5
<212> TYPE: PRT
<213> ORGANISM: Mus musculus

<400> SEQUENCE: 66

Lys Tyr Val Ile His
1               5

<210> SEQ ID NO 67
<211> LENGTH: 17
<212> TYPE: PRT
<213> ORGANISM: Mus musculus

<400> SEQUENCE: 67

Tyr Ile Asn Pro Tyr Asn Asp Val Ser Lys Tyr Asn Glu Lys Phe Arg
1               5                   10                  15
Gly

<210> SEQ ID NO 68
<211> LENGTH: 9
<212> TYPE: PRT
<213> ORGANISM: Mus musculus

<400> SEQUENCE: 68

Asn Lys Asp Tyr Tyr Pro Met Asp Tyr
1               5

<210> SEQ ID NO 69
<211> LENGTH: 11
<212> TYPE: PRT
<213> ORGANISM: Mus musculus

<400> SEQUENCE: 69

Ser Ala Ser Ser Ser Val Arg Phe Ile His Trp
1               5                   10

<210> SEQ ID NO 70
<211> LENGTH: 7
<212> TYPE: PRT
<213> ORGANISM: Mus musculus

<400> SEQUENCE: 70

Asp Thr Ser Lys Leu Ala Ser
1               5
```

<210> SEQ ID NO 71
<211> LENGTH: 9
<212> TYPE: PRT
<213> ORGANISM: Mus musculus

<400> SEQUENCE: 71

Gln Gln Trp Ser Ser Ser Pro Phe Thr
1               5

<210> SEQ ID NO 72
<211> LENGTH: 6
<212> TYPE: PRT
<213> ORGANISM: Mus musculus

<400> SEQUENCE: 72

Asp Tyr Tyr Ile His Trp
1               5

<210> SEQ ID NO 73
<211> LENGTH: 17
<212> TYPE: PRT
<213> ORGANISM: Mus musculus

<400> SEQUENCE: 73

Trp Ile Asp Pro Glu Asn Gly Asp Thr Glu Phe Val Pro Lys Phe Gln
1               5                   10                  15

Gly

<210> SEQ ID NO 74
<211> LENGTH: 4
<212> TYPE: PRT
<213> ORGANISM: Mus musculus

<400> SEQUENCE: 74

Thr Gly Gly Phe
1

<210> SEQ ID NO 75
<211> LENGTH: 10
<212> TYPE: PRT
<213> ORGANISM: Homo sapiens

<400> SEQUENCE: 75

Lys Pro Leu Pro Glu Val Thr Asp Glu Tyr
1               5                   10

<210> SEQ ID NO 76
<211> LENGTH: 18
<212> TYPE: PRT
<213> ORGANISM: Homo sapiens

<400> SEQUENCE: 76

Glu Lys Glu Ala Leu Lys Lys Ile Ile Glu Asp Gln Gln Glu Ser Leu
1               5                   10                  15

Asn Lys

<210> SEQ ID NO 77
<211> LENGTH: 408
<212> TYPE: PRT
<213> ORGANISM: Homo sapiens

<400> SEQUENCE: 77

```
Met Ala Glu Asn Gly Asp Asn Glu Lys Met Ala Ala Leu Glu Ala Lys
1               5                   10                  15

Ile Cys His Gln Ile Glu Tyr Tyr Phe Gly Asp Phe Asn Leu Pro Arg
            20                  25                  30

Asp Lys Phe Leu Lys Glu Gln Ile Lys Leu Asp Glu Gly Trp Val Pro
                35                  40                  45

Leu Glu Ile Met Ile Lys Phe Asn Arg Leu Asn Arg Leu Thr Thr Asp
50                  55                  60

Phe Asn Val Ile Val Glu Ala Leu Ser Lys Ser Lys Ala Glu Leu Met
65                  70                  75                  80

Glu Ile Ser Glu Asp Lys Thr Lys Ile Arg Arg Ser Pro Ser Lys Pro
                85                  90                  95

Leu Pro Glu Val Thr Asp Glu Tyr Lys Asn Asp Val Lys Asn Arg Ser
                100                 105                 110

Val Tyr Ile Lys Gly Phe Pro Thr Asp Ala Thr Leu Asp Asp Ile Lys
            115                 120                 125

Glu Trp Leu Glu Asp Lys Gly Gln Val Leu Asn Ile Gln Met Arg Arg
            130                 135                 140

Thr Leu His Lys Ala Phe Lys Gly Ser Ile Phe Val Val Phe Asp Ser
145                 150                 155                 160

Ile Glu Ser Ala Lys Lys Phe Val Glu Thr Pro Gly Gln Lys Tyr Lys
                165                 170                 175

Glu Thr Asp Leu Leu Ile Leu Phe Lys Asp Asp Tyr Phe Ala Lys Lys
            180                 185                 190

Asn Glu Glu Arg Lys Gln Asn Lys Val Glu Ala Lys Leu Arg Ala Lys
            195                 200                 205

Gln Glu Gln Glu Ala Lys Gln Lys Leu Glu Glu Asp Ala Glu Met Lys
            210                 215                 220

Ser Leu Glu Glu Lys Ile Gly Cys Leu Leu Lys Phe Ser Gly Asp Leu
225                 230                 235                 240

Asp Asp Gln Thr Cys Arg Glu Asp Leu His Ile Leu Phe Ser Asn His
                245                 250                 255

Gly Glu Ile Lys Trp Ile Asp Phe Val Arg Gly Ala Lys Glu Gly Ile
            260                 265                 270

Ile Leu Phe Lys Glu Lys Ala Lys Glu Ala Leu Gly Lys Ala Lys Asp
            275                 280                 285

Ala Asn Asn Gly Asn Leu Gln Leu Arg Asn Lys Glu Val Thr Trp Glu
            290                 295                 300

Val Leu Glu Gly Glu Val Glu Lys Glu Ala Leu Lys Lys Ile Ile Glu
305                 310                 315                 320

Asp Gln Gln Glu Ser Leu Asn Lys Trp Lys Ser Lys Gly Arg Arg Phe
                325                 330                 335

Lys Gly Lys Gly Lys Gly Asn Lys Ala Ala Gln Pro Gly Ser Gly Lys
            340                 345                 350

Gly Lys Val Gln Phe Gln Gly Lys Lys Thr Lys Phe Ala Ser Asp Asp
            355                 360                 365

Glu His Asp Glu His Asp Glu Asn Gly Ala Thr Gly Pro Val Lys Arg
            370                 375                 380

Ala Arg Glu Glu Thr Asp Lys Glu Glu Pro Ala Ser Lys Gln Gln Lys
385                 390                 395                 400

Thr Glu Asn Gly Ala Gly Asp Gln
            405
```

```
<210> SEQ ID NO 78
<211> LENGTH: 17
<212> TYPE: PRT
<213> ORGANISM: Mus musculus

<400> SEQUENCE: 78

Lys Ser Ser Gln Ser Leu Leu Asn Ser Arg Thr Pro Lys Asn Tyr Leu
1               5                   10                  15
Ala

<210> SEQ ID NO 79
<211> LENGTH: 7
<212> TYPE: PRT
<213> ORGANISM: Mus musculus

<400> SEQUENCE: 79

Trp Ala Ser Thr Arg Lys Ser
1               5

<210> SEQ ID NO 80
<211> LENGTH: 8
<212> TYPE: PRT
<213> ORGANISM: Mus musculus

<400> SEQUENCE: 80

Lys Gln Ser Tyr Asn Leu Leu Thr
1               5

<210> SEQ ID NO 81
<211> LENGTH: 5
<212> TYPE: PRT
<213> ORGANISM: Mus musculus

<400> SEQUENCE: 81

His Tyr Tyr Ile Tyr
1               5

<210> SEQ ID NO 82
<211> LENGTH: 17
<212> TYPE: PRT
<213> ORGANISM: Mus musculus

<400> SEQUENCE: 82

Gly Val Asn Pro Ser Asn Gly Gly Thr His Phe Asn Glu Lys Phe Lys
1               5                   10                  15
Ser

<210> SEQ ID NO 83
<211> LENGTH: 11
<212> TYPE: PRT
<213> ORGANISM: Mus musculus

<400> SEQUENCE: 83

Ser Glu Tyr Asp Tyr Gly Leu Gly Phe Ala Tyr
1               5                   10

<210> SEQ ID NO 84
<211> LENGTH: 17
<212> TYPE: PRT
<213> ORGANISM: Mus musculus

<400> SEQUENCE: 84

Arg Ser Ser Gln Ser Leu Leu Asp Ser Arg Thr Arg Lys Asn Tyr Leu
1               5                   10                  15
```

Ala

<210> SEQ ID NO 85
<211> LENGTH: 7
<212> TYPE: PRT
<213> ORGANISM: Mus musculus

<400> SEQUENCE: 85

Trp Ala Ser Thr Arg Glu Ser
1               5

<210> SEQ ID NO 86
<211> LENGTH: 8
<212> TYPE: PRT
<213> ORGANISM: Mus musculus

<400> SEQUENCE: 86

Lys Gln Ser Tyr Asn Leu Pro Thr
1               5

<210> SEQ ID NO 87
<211> LENGTH: 5
<212> TYPE: PRT
<213> ORGANISM: Mus musculus

<400> SEQUENCE: 87

Asp Phe Trp Met Asn
1               5

<210> SEQ ID NO 88
<211> LENGTH: 19
<212> TYPE: PRT
<213> ORGANISM: Mus musculus

<400> SEQUENCE: 88

Gln Ile Arg Asn Lys Pro Asn Asn Tyr Glu Thr Tyr Tyr Ser Asp Ser
1               5                   10                  15

Leu Lys Gly

<210> SEQ ID NO 89
<211> LENGTH: 8
<212> TYPE: PRT
<213> ORGANISM: Mus musculus

<400> SEQUENCE: 89

Leu Gly Asn Ser Trp Phe Ala Tyr
1               5

<210> SEQ ID NO 90
<211> LENGTH: 34
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(17)
<223> OTHER INFORMATION: n is a, c, g, or t

<400> SEQUENCE: 90
tttttggatc csargtnmag ctgsagsagt cwgg                              34

<210> SEQ ID NO 91
<211> LENGTH: 30

<212> TYPE: DNA
<213> ORGANISM: Artificial Sequence
<220> FEATURE:
<223> OTHER INFORMATION: Primer

<400> SEQUENCE: 91
ggaagatcta tagacagatg ggggtgtcgt                                    30

<210> SEQ ID NO 92
<211> LENGTH: 36
<212> TYPE: DNA
<213> ORGANISM: Artificial Sequence
<220> FEATURE:
<223> OTHER INFORMATION: Primer

<400> SEQUENCE: 92
tttttgaatt ctgayattgt gmtsacmcar wctmca                              36

<210> SEQ ID NO 93
<211> LENGTH: 32
<212> TYPE: DNA
<213> ORGANISM: Artificial Sequence
<220> FEATURE:
<223> OTHER INFORMATION: Primer

<400> SEQUENCE: 93
tttttgggcc cggatacagt tggtgcagca tc                                  32

<210> SEQ ID NO 94
<211> LENGTH: 51
<212> TYPE: DNA
<213> ORGANISM: Artificial Sequence
<220> FEATURE:
<223> OTHER INFORMATION: Primer

<400> SEQUENCE: 94
ggcccagccg gccatggcgg actacaaaga agtacagctg caggagtcag g             51

<210> SEQ ID NO 95
<211> LENGTH: 50
<212> TYPE: DNA
<213> ORGANISM: Artificial Sequence
<220> FEATURE:
<223> OTHER INFORMATION: Primer

<400> SEQUENCE: 95
ggagccgccg ccgccagaac caccaccacc tgaggagacg gtgaccgtgg               50

<210> SEQ ID NO 96
<211> LENGTH: 53
<212> TYPE: DNA
<213> ORGANISM: Artificial Sequence
<220> FEATURE:
<223> OTHER INFORMATION: Primer

<400> SEQUENCE: 96
ggcggcggcg gctccggtgg tggtggatcc gatattgtga tgacacagtc tac           53

<210> SEQ ID NO 97
<211> LENGTH: 29
<212> TYPE: DNA
<213> ORGANISM: Artificial Sequence
<220> FEATURE:
<223> OTHER INFORMATION: Primer

<400> SEQUENCE: 97

-continued

```
gcggccgcgg atacagttgg tgcagcatc                                       29

<210> SEQ ID NO 98
<211> LENGTH: 39
<212> TYPE: DNA
<213> ORGANISM: Artificial Sequence
<220> FEATURE:
<223> OTHER INFORMATION: Primer

<400> SEQUENCE: 98
gggcccgaat tcatggcgga ctacaaagag gtgcagctg                            39

<210> SEQ ID NO 99
<211> LENGTH: 39
<212> TYPE: DNA
<213> ORGANISM: Artificial Sequence
<220> FEATURE:
<223> OTHER INFORMATION: Primer

<400> SEQUENCE: 99
gggcccaagc ttggatacag ttggtgcagc atcagcccg                            39

<210> SEQ ID NO 100
<211> LENGTH: 100
<212> TYPE: DNA
<213> ORGANISM: Artificial Sequence
<220> FEATURE:
<223> OTHER INFORMATION: Oligonucleotide

<400> SEQUENCE: 100
caggttcagc tggtgcagtc tggagctgag gtgaagaagc ctggggcctc agtgaaggtc     60
tcctgtaagg cttctggtta caccttacc aaatatgtta                           100

<210> SEQ ID NO 101
<211> LENGTH: 100
<212> TYPE: DNA
<213> ORGANISM: Artificial Sequence
<220> FEATURE:
<223> OTHER INFORMATION: Oligonucleotide

<400> SEQUENCE: 101
acatcattgt aaggattaat atatcccatc cactcaagcc cttgtccagg ggcctgtcgc     60
acccaatgta taacatattt ggtaaaggtg taaccagaag                          100

<210> SEQ ID NO 102
<211> LENGTH: 100
<212> TYPE: DNA
<213> ORGANISM: Artificial Sequence
<220> FEATURE:
<223> OTHER INFORMATION: Oligonucleotide

<400> SEQUENCE: 102
gatgggatat attaatcctt acaatgatgt tagtaagtac aatgagaagt tcagaggcag     60
agtcaccatg accacagaca catccacgag cacagcctac                          100

<210> SEQ ID NO 103
<211> LENGTH: 100
<212> TYPE: DNA
<213> ORGANISM: Artificial Sequence
<220> FEATURE:
<223> OTHER INFORMATION: Oligonucleotide

<400> SEQUENCE: 103
gatagtaatc cttatttctc gcacagtaat acacggccgt gtcgtcagat ctcaggctcc     60
```

```
tcagctccat gtaggctgtg ctcgtggatg tgtctgtggt                            100
```

<210> SEQ ID NO 104
<211> LENGTH: 86
<212> TYPE: DNA
<213> ORGANISM: Artificial Sequence
<220> FEATURE:
<223> OTHER INFORMATION: Oligonucleotide

<400> SEQUENCE: 104

```
attactgtgc gagaaataag gattactatc ctatggacta ctggggccaa gggaccacgg       60
tcaccgtctc gggaggagga ggatcc                                           86
```

<210> SEQ ID NO 105
<211> LENGTH: 37
<212> TYPE: DNA
<213> ORGANISM: Artificial Sequence
<220> FEATURE:
<223> OTHER INFORMATION: Primer

<400> SEQUENCE: 105

```
ggcccagccg gcccaggttc agctggtgca gtctgga                               37
```

<210> SEQ ID NO 106
<211> LENGTH: 39
<212> TYPE: DNA
<213> ORGANISM: Artificial Sequence
<220> FEATURE:
<223> OTHER INFORMATION: Primer

<400> SEQUENCE: 106

```
ggatcctcct cctcccgaga cggtgaccgt ggtcccttg                             39
```

<210> SEQ ID NO 107
<211> LENGTH: 90
<212> TYPE: DNA
<213> ORGANISM: Artificial Sequence
<220> FEATURE:
<223> OTHER INFORMATION: Oligonucleotide

<400> SEQUENCE: 107

```
gaaattgtgt tgacacagtc tccagccacc ctgtctttgt ctccagggga aagagccacc      60
ctctcctgca gtgccagttc aagtgtaagt                                       90
```

<210> SEQ ID NO 108
<211> LENGTH: 91
<212> TYPE: DNA
<213> ORGANISM: Artificial Sequence
<220> FEATURE:
<223> OTHER INFORMATION: Oligonucleotide

<400> SEQUENCE: 108

```
tgtgtcatag atgaggagcc tgggagcctg gccaggtttc tgttggtacc agtgcatgta      60
acttacactt gaactggcac tgcaggagag g                                     91
```

<210> SEQ ID NO 109
<211> LENGTH: 91
<212> TYPE: DNA
<213> ORGANISM: Artificial Sequence
<220> FEATURE:
<223> OTHER INFORMATION: Oligonucleotide

<400> SEQUENCE: 109

```
ccaggctccc aggctcctca tctatgacac atccaaactg gcttctggca tcccagccag    60
gttcagtggc agtgggtctg ggacagactt c                                   91
```

<210> SEQ ID NO 110
<211> LENGTH: 91
<212> TYPE: DNA
<213> ORGANISM: Artificial Sequence
<220> FEATURE:
<223> OTHER INFORMATION: Oligonucleotide

<400> SEQUENCE: 110

```
ccactgctga cagtaataaa ctgcaaaatc ttcaggctct aggctgctga tggtgagagt    60
gaagtctgtc ccagacccac tgccactgaa c                                   91
```

<210> SEQ ID NO 111
<211> LENGTH: 79
<212> TYPE: DNA
<213> ORGANISM: Artificial Sequence
<220> FEATURE:
<223> OTHER INFORMATION: Oligonucleotide

<400> SEQUENCE: 111

```
agattttgca gtttattact gtcagcagtg gagtagtaac ccgctcacgt tcggcggagg    60
gaccaaggtg gagatcaaa                                                 79
```

<210> SEQ ID NO 112
<211> LENGTH: 27
<212> TYPE: DNA
<213> ORGANISM: Artificial Sequence
<220> FEATURE:
<223> OTHER INFORMATION: Primer

<400> SEQUENCE: 112

```
ggatccgaaa ttgtgttgac acagtct                                        27
```

<210> SEQ ID NO 113
<211> LENGTH: 29
<212> TYPE: DNA
<213> ORGANISM: Artificial Sequence
<220> FEATURE:
<223> OTHER INFORMATION: Primer

<400> SEQUENCE: 113

```
gcggccgctt tgatctccac cttggtccc                                      29
```

<210> SEQ ID NO 114
<211> LENGTH: 50
<212> TYPE: DNA
<213> ORGANISM: Artificial Sequence
<220> FEATURE:
<223> OTHER INFORMATION: Primer

<400> SEQUENCE: 114

```
ggatccgccg ccgccagaac caccaccacc ggagcctcct cctcccgaga               50
```

<210> SEQ ID NO 115
<211> LENGTH: 100
<212> TYPE: DNA
<213> ORGANISM: Artificial Sequence
<220> FEATURE:
<223> OTHER INFORMATION: Oligonucleotide

<400> SEQUENCE: 115

```
gatatccaga tgactcaaag tcctagttcc ctgtctgcat cagtgggaga ccgggtgacc    60
```

```
attacatgcg gtacatccca agacatcaat aattatctca                              100
```

<210> SEQ ID NO 116
<211> LENGTH: 100
<212> TYPE: DNA
<213> ORGANISM: Artificial Sequence
<220> FEATURE:
<223> OTHER INFORMATION: Oligonucleotide

<400> SEQUENCE: 116

```
cggaatgcag cctggatgtg tagtagatta ataacttagg aactttgcct ggcttctgct    60
gataccagtt gagataatta ttgatgtctt gggatgtacc                          100
```

<210> SEQ ID NO 117
<211> LENGTH: 100
<212> TYPE: DNA
<213> ORGANISM: Artificial Sequence
<220> FEATURE:
<223> OTHER INFORMATION: Oligonucleotide

<400> SEQUENCE: 117

```
aatctactac acatccaggc tgcattccgg ggtgccctcc cgcttttcgg gctccgggtc    60
gggaaccgac tttaccctaa ccatatcttc cctgcagcct                          100
```

<210> SEQ ID NO 118
<211> LENGTH: 111
<212> TYPE: DNA
<213> ORGANISM: Artificial Sequence
<220> FEATURE:
<223> OTHER INFORMATION: Oligonucleotide

<400> SEQUENCE: 118

```
aagtacagtg agttgcgtcc caccaccaaa tgtccatggt aatgtctttg actgctgaca    60
atagtacgtt gcaacgtctt caggctgcag ggaagatatg gttagggtaa a            111
```

<210> SEQ ID NO 119
<211> LENGTH: 29
<212> TYPE: DNA
<213> ORGANISM: Artificial Sequence
<220> FEATURE:
<223> OTHER INFORMATION: Primer

<400> SEQUENCE: 119

```
ctcgaggaga tatccagatg actcaaagt                                       29
```

<210> SEQ ID NO 120
<211> LENGTH: 57
<212> TYPE: DNA
<213> ORGANISM: Artificial Sequence
<220> FEATURE:
<223> OTHER INFORMATION: Primer

<400> SEQUENCE: 120

```
agcggcactt gctccgctcc ctcctccacc actgccacct ccaccaagta cagtgag       57
```

<210> SEQ ID NO 121
<211> LENGTH: 100
<212> TYPE: DNA
<213> ORGANISM: Artificial Sequence
<220> FEATURE:
<223> OTHER INFORMATION: Oligonucleotide

<400> SEQUENCE: 121

```
caggtgcagc tagtggagtc cggtggcggc ctcgttaagc cgggcggatc gctgcgcctt    60
tcatgtgccg catcaggatt cacattctcc agttactcta                        100
```

<210> SEQ ID NO 122
<211> LENGTH: 100
<212> TYPE: DNA
<213> ORGANISM: Artificial Sequence
<220> FEATURE:
<223> OTHER INFORMATION: Oligonucleotide

<400> SEQUENCE: 122

```
cttccacctg aatcattaat gtacgagacc cattccaatc ccttgccagg tgcctgccga    60
atccatgaca tagagtaact ggagaatgtg aatcctgatg                        100
```

<210> SEQ ID NO 123
<211> LENGTH: 100
<212> TYPE: DNA
<213> ORGANISM: Artificial Sequence
<220> FEATURE:
<223> OTHER INFORMATION: Oligonucleotide

<400> SEQUENCE: 123

```
ggtctcgtac attaatgatt caggtggaag tacattctat ccggacacgg ttaaaggtag    60
atttaccatc agccgtgata acgcgaagaa tagcttgtac                        100
```

<210> SEQ ID NO 124
<211> LENGTH: 100
<212> TYPE: DNA
<213> ORGANISM: Artificial Sequence
<220> FEATURE:
<223> OTHER INFORMATION: Oligonucleotide

<400> SEQUENCE: 124

```
tgccataata catacgtcga gcgcaataat atacagcagt atcctctgca cgcaggctat    60
tcatctgtaa gtacaagcta ttcttcgcgt tatcacggct                        100
```

<210> SEQ ID NO 125
<211> LENGTH: 86
<212> TYPE: DNA
<213> ORGANISM: Artificial Sequence
<220> FEATURE:
<223> OTHER INFORMATION: Oligonucleotide

<400> SEQUENCE: 125

```
attattgcgc tcgacgtatg tattatggca atagtcactg gcactttgac gtctggggcc    60
agggcacgac agttactgtc tcttcg                                        86
```

<210> SEQ ID NO 126
<211> LENGTH: 58
<212> TYPE: DNA
<213> ORGANISM: Artificial Sequence
<220> FEATURE:
<223> OTHER INFORMATION: Primer

<400> SEQUENCE: 126

```
ggagcaagtg ccgctggagg cggaggttca ggcggtggtg aagccaggt gcagctag      58
```

<210> SEQ ID NO 127
<211> LENGTH: 27
<212> TYPE: DNA
<213> ORGANISM: Artificial Sequence
<220> FEATURE:
<223> OTHER INFORMATION: Primer -continued

<400> SEQUENCE: 127 gggcccccgaa gagacagtaa ctgtcgt                27

<210> SEQ ID NO 128
<211> LENGTH: 29
<212> TYPE: DNA
<213> ORGANISM: Artificial Sequence
<220> FEATURE:
<223> OTHER INFORMATION: Primer

<400> SEQUENCE: 128
ctcgaggaga tatccagatg actcaaagt                29

<210> SEQ ID NO 129
<211> LENGTH: 27
<212> TYPE: DNA
<213> ORGANISM: Artificial Sequence
<220> FEATURE:
<223> OTHER INFORMATION: Primer

<400> SEQUENCE: 129 gggcccccgaa gagacagtaa ctgtcgt                27

<210> SEQ ID NO 130
<211> LENGTH: 25
<212> TYPE: PRT
<213> ORGANISM: Artificial Sequence
<220> FEATURE:
<223> OTHER INFORMATION: Peptide

<400> SEQUENCE: 130

Gly Gly Gly Gly Ser Gly Gly Gly Gly Ser Gly Ala Ser Ala Ala Gly
1               5                   10                  15

Gly Gly Gly Ser Gly Gly Gly Gly Ser
            20                  25

<210> SEQ ID NO 131
<211> LENGTH: 15
<212> TYPE: PRT
<213> ORGANISM: Artificial Sequence
<220> FEATURE:
<223> OTHER INFORMATION: Peptide

<400> SEQUENCE: 131

Gly Gly Gly Gly Ser Gly Gly Gly Gly Ser Gly Gly Gly Gly Ser
1               5                   10                  15

<210> SEQ ID NO 132
<211> LENGTH: 5
<212> TYPE: PRT
<213> ORGANISM: Artificial Sequence
<220> FEATURE:
<223> OTHER INFORMATION: Peptide

<400> SEQUENCE: 132

Gly Gly Gly Gly Ser
1               5

<210> SEQ ID NO 133
<211> LENGTH: 5
<212> TYPE: PRT
<213> ORGANISM: Artificial Sequence
<220> FEATURE:
<223> OTHER INFORMATION: Peptide

<400> SEQUENCE: 133

Ala Ala Ala Arg Gly
1               5

<210> SEQ ID NO 134
<211> LENGTH: 40
<212> TYPE: DNA
<213> ORGANISM: Artificial Sequence
<220> FEATURE:
<223> OTHER INFORMATION: Primer

<400> SEQUENCE: 134
ggcccagccg gccggatccg atatccagat gactcaaagt                          40

<210> SEQ ID NO 135
<211> LENGTH: 41
<212> TYPE: DNA
<213> ORGANISM: Artificial Sequence
<220> FEATURE:
<223> OTHER INFORMATION: Primer

<400> SEQUENCE: 135
gcggccgcgg atcctcctcc tcccgaagag acagtaactg t                        41

<210> SEQ ID NO 136
<211> LENGTH: 39
<212> TYPE: DNA
<213> ORGANISM: Artificial Sequence
<220> FEATURE:
<223> OTHER INFORMATION: Oligonucleotide

<400> SEQUENCE: 136
ggccgctaaa cccctacctg aagtgactga tgagtatgc                           39

<210> SEQ ID NO 137
<211> LENGTH: 39
<212> TYPE: DNA
<213> ORGANISM: Artificial Sequence
<220> FEATURE:
<223> OTHER INFORMATION: Oligonucleotide

<400> SEQUENCE: 137
tcgagcatac tcatcagtca cttcaggtag gggtttagc                           39

<210> SEQ ID NO 138
<211> LENGTH: 100
<212> TYPE: DNA
<213> ORGANISM: Artificial Sequence
<220> FEATURE:
<223> OTHER INFORMATION: Oligonucleotide

<400> SEQUENCE: 138
caagtgcaac tggtccagtc aggtgctgag gtgaaaaaac ccggagccag tgtcaaagta    60
agctgcaagg cctctgggta tactttcacc cattactata                         100

<210> SEQ ID NO 139
<211> LENGTH: 100
<212> TYPE: DNA
<213> ORGANISM: Artificial Sequence
<220> FEATURE:
<223> OTHER INFORMATION: Oligonucleotide

<400> SEQUENCE: 139
ccaccgttcg aagggttgac tccacccatc cactcaagcc cctgacctgg agcttgacga    60

```
acccagtata tatagtaatg ggtgaaagta tacccagagg                    100
```

<210> SEQ ID NO 140
<211> LENGTH: 100
<212> TYPE: DNA
<213> ORGANISM: Artificial Sequence
<220> FEATURE:
<223> OTHER INFORMATION: Oligonucleotide

<400> SEQUENCE: 140

```
gatgggtgga gtcaacccatt cgaacggtgg cactcacttc aatgaaaagt ttaaaagccg    60
cgtaaccatg acgcgagata cttccatttc cacagcttat                   100
```

<210> SEQ ID NO 141
<211> LENGTH: 100
<212> TYPE: DNA
<213> ORGANISM: Artificial Sequence
<220> FEATURE:
<223> OTHER INFORMATION: Oligonucleotide

<400> SEQUENCE: 141

```
cataatcata ttcacttcta gcacagtaat aaacggccgt gtcatcactg cgtaacctac    60
taagttccat ataagctgtg gaaatggaag tatctcgcgt                   100
```

<210> SEQ ID NO 142
<211> LENGTH: 80
<212> TYPE: DNA
<213> ORGANISM: Artificial Sequence
<220> FEATURE:
<223> OTHER INFORMATION: Oligonucleotide

<400> SEQUENCE: 142

```
attactgtgc tagaagtgaa tatgattatg ggttgggttt cgcttactgg ggccagggaa    60
ccctcgtcac cgtgtccagt                                          80
```

<210> SEQ ID NO 143
<211> LENGTH: 33
<212> TYPE: DNA
<213> ORGANISM: Artificial Sequence
<220> FEATURE:
<223> OTHER INFORMATION: Primer

<400> SEQUENCE: 143

```
ctcgaggaca agtgcaactg gtccagtcag gtg                            33
```

<210> SEQ ID NO 144
<211> LENGTH: 55
<212> TYPE: DNA
<213> ORGANISM: Artificial Sequence
<220> FEATURE:
<223> OTHER INFORMATION: Primer

<400> SEQUENCE: 144

```
agaaccgcca ccaccggatc ctccaccacc actggacacg gtgacgaggg ttccc         55
```

<210> SEQ ID NO 145
<211> LENGTH: 100
<212> TYPE: DNA
<213> ORGANISM: Artificial Sequence
<220> FEATURE:
<223> OTHER INFORMATION: Oligonucleotide

<400> SEQUENCE: 145

```
gacattgtta tgacgcagag ccctgattca ctcgcagtgt ccctaggaga gcgggccacc    60
```

```
atcaactgta aaagttctca gtccctgctg aacagcagga                          100
```

<210> SEQ ID NO 146
<211> LENGTH: 100
<212> TYPE: DNA
<213> ORGANISM: Artificial Sequence
<220> FEATURE:
<223> OTHER INFORMATION: Oligonucleotide

<400> SEQUENCE: 146

```
gcccagtaaa tgagcagctt aggcggctgt ccaggtttct gttggtacca tgccaggtaa    60
ttcttaggcg tcctgctgtt cagcagggac tgagaacttt                         100
```

<210> SEQ ID NO 147
<211> LENGTH: 100
<212> TYPE: DNA
<213> ORGANISM: Artificial Sequence
<220> FEATURE:
<223> OTHER INFORMATION: Oligonucleotide

<400> SEQUENCE: 147

```
acagccgcct aagctgctca tttactgggc ctccacacgg aagagcggcg tgcccgaccg    60
gttttccggg agcggctccg gcaccgactt taccttgacc                         100
```

<210> SEQ ID NO 148
<211> LENGTH: 100
<212> TYPE: DNA
<213> ORGANISM: Artificial Sequence
<220> FEATURE:
<223> OTHER INFORMATION: Oligonucleotide

<400> SEQUENCE: 148

```
caaatgtcag gagattgtaa gattgcttgc aatagtatac ggccacgtct tctgcctgca    60
gggaactgat ggtcaaggta aagtcggtgc cggagccgct                         100
```

<210> SEQ ID NO 149
<211> LENGTH: 56
<212> TYPE: DNA
<213> ORGANISM: Artificial Sequence
<220> FEATURE:
<223> OTHER INFORMATION: Oligonucleotide

<400> SEQUENCE: 149

```
gcaagcaatc ttacaatctc ctgacatttg gcggcggcac aaaagtggag atcaaa         56
```

<210> SEQ ID NO 150
<211> LENGTH: 55
<212> TYPE: DNA
<213> ORGANISM: Artificial Sequence
<220> FEATURE:
<223> OTHER INFORMATION: Primer

<400> SEQUENCE: 150

```
ggtggtggcg gttctggcgg aggcggatcc gacattgtta tgacgcagag ccctg          55
```

<210> SEQ ID NO 151
<211> LENGTH: 31
<212> TYPE: DNA
<213> ORGANISM: Artificial Sequence
<220> FEATURE:
<223> OTHER INFORMATION: Primer

<400> SEQUENCE: 151

```
gggcccttcg atctccactt ttgtgccgcc g                                    31
```

<210> SEQ ID NO 152
<211> LENGTH: 33
<212> TYPE: DNA
<213> ORGANISM: Artificial Sequence
<220> FEATURE:
<223> OTHER INFORMATION: Primer

<400> SEQUENCE: 152

```
ctcgaggaca agtgcaactg gtccagtcag gtg                                  33
```

<210> SEQ ID NO 153
<211> LENGTH: 31
<212> TYPE: DNA
<213> ORGANISM: Artificial Sequence
<220> FEATURE:
<223> OTHER INFORMATION: Primer

<400> SEQUENCE: 153

```
gggcccttcg atctccactt ttgtgccgcc g                                    31
```

<210> SEQ ID NO 154
<211> LENGTH: 72
<212> TYPE: DNA
<213> ORGANISM: Artificial Sequence
<220> FEATURE:
<223> OTHER INFORMATION: Oligonucleotide

<400> SEQUENCE: 154

```
ggccgctctg gagaaagaag cactgaagaa aataatagaa gaccaacaag aatccctaaa     60
caaagcagct gc                                                         72
```

<210> SEQ ID NO 155
<211> LENGTH: 72
<212> TYPE: DNA
<213> ORGANISM: Artificial Sequence
<220> FEATURE:
<223> OTHER INFORMATION: Oligonucleotide

<400> SEQUENCE: 155

```
tcgagcagct gctttgttta gggattcttg ttggtcttct attattttct tcagtgcttc     60
tttctccaga gc                                                         72
```

<210> SEQ ID NO 156
<211> LENGTH: 100
<212> TYPE: DNA
<213> ORGANISM: Artificial Sequence
<220> FEATURE:
<223> OTHER INFORMATION: Oligonucleotide

<400> SEQUENCE: 156

```
gaggtgcaac tggtcgaaag tggcggtggt ttagttcagc ctggtggaag tctacggctt     60
agctgcgcag catccggttt cacctttagc gacttttgga                          100
```

<210> SEQ ID NO 157
<211> LENGTH: 100
<212> TYPE: DNA
<213> ORGANISM: Artificial Sequence
<220> FEATURE:
<223> OTHER INFORMATION: Oligonucleotide

<400> SEQUENCE: 157

```
ttattcggtt tgttgcggat tgcccaacc cactccagtc ctttgcccgg agcctgccga      60
```

```
acccagttca tccaaaagtc gctaaaggtg aaaccggatg                          100
```

<210> SEQ ID NO 158
<211> LENGTH: 100
<212> TYPE: DNA
<213> ORGANISM: Artificial Sequence
<220> FEATURE:
<223> OTHER INFORMATION: Oligonucleotide

<400> SEQUENCE: 158

```
ggttgggcaa atccgcaaca aaccgaataa ctacgaaact tattactcag atagcctgaa   60
gggtcgattc accatcagca gggatgattc aaagtcaatc                        100
```

<210> SEQ ID NO 159
<211> LENGTH: 100
<212> TYPE: DNA
<213> ORGANISM: Artificial Sequence
<220> FEATURE:
<223> OTHER INFORMATION: Oligonucleotide

<400> SEQUENCE: 159

```
aggagttacc tagtgtacag taatacaccg cagtatcctc cgctcttaat gagttcatct   60
gtaggtaagt gattgacttt gaatcatccc tgctgatggt                        100
```

<210> SEQ ID NO 160
<211> LENGTH: 74
<212> TYPE: DNA
<213> ORGANISM: Artificial Sequence
<220> FEATURE:
<223> OTHER INFORMATION: Oligonucleotide

<400> SEQUENCE: 160

```
cggtgtatta ctgtacacta ggtaactcct ggttcgcgta ttggggacag ggcacccttg   60
taaccgtctc cagc                                                    74
```

<210> SEQ ID NO 161
<211> LENGTH: 65
<212> TYPE: DNA
<213> ORGANISM: Artificial Sequence
<220> FEATURE:
<223> OTHER INFORMATION: Primer

<400> SEQUENCE: 161

```
ggtggcggcg gctccggagg tggtggttcc ggcggtggcg gatcggaggt gcaactggtc   60
gaaag                                                              65
```

<210> SEQ ID NO 162
<211> LENGTH: 27
<212> TYPE: DNA
<213> ORGANISM: Artificial Sequence
<220> FEATURE:
<223> OTHER INFORMATION: Primer

<400> SEQUENCE: 162

```
gggcccgctg gagacggtta caagggt                                      27
```

<210> SEQ ID NO 163
<211> LENGTH: 100
<212> TYPE: DNA
<213> ORGANISM: Artificial Sequence
<220> FEATURE:
<223> OTHER INFORMATION: Oligonucleotide

<400> SEQUENCE: 163
gacattgtta tgacccagag cccggactct ctcgctgtta gtcttggtga gcgagcgact    60
attaactgcc ggagcagtca gagtttgttg gactcacgga    100

<210> SEQ ID NO 164
<211> LENGTH: 100
<212> TYPE: DNA
<213> ORGANISM: Artificial Sequence
<220> FEATURE:
<223> OTHER INFORMATION: Oligonucleotide

<400> SEQUENCE: 164
gcccaatata tcagtaattt aggtggttgg cccggcttct gctggtacca tgccaggtag    60
ttctttctcg tccgtgagtc aacaaactc tgactgctcc    100

<210> SEQ ID NO 165
<211> LENGTH: 100
<212> TYPE: DNA
<213> ORGANISM: Artificial Sequence
<220> FEATURE:
<223> OTHER INFORMATION: Oligonucleotide

<400> SEQUENCE: 165
ccaaccacct aaattactga tatattgggc gtcgactcgt gagtcagggg taccggacag    60
gttttctgga agcggatcag gaacagactt cactttgacg    100

<210> SEQ ID NO 166
<211> LENGTH: 100
<212> TYPE: DNA
<213> ORGANISM: Artificial Sequence
<220> FEATURE:
<223> OTHER INFORMATION: Oligonucleotide

<400> SEQUENCE: 166
caaatgtcgg cagattatag ctttgcttac aataataaac cgcaacgtcc tcggcttgaa    60
gcgaagagat cgtcaaagtg aagtctgttc ctgatccgct    100

<210> SEQ ID NO 167
<211> LENGTH: 56
<212> TYPE: DNA
<213> ORGANISM: Artificial Sequence
<220> FEATURE:
<223> OTHER INFORMATION: Oligonucleotide

<400> SEQUENCE: 167
gtaagcaaag ctataatctg ccgacatttg gtggcggcac caaggttgaa attaag    56

<210> SEQ ID NO 168
<211> LENGTH: 29
<212> TYPE: DNA
<213> ORGANISM: Artificial Sequence
<220> FEATURE:
<223> OTHER INFORMATION: Primer

<400> SEQUENCE: 168
ctcgaggaga cattgttatg acccagagc    29

<210> SEQ ID NO 169
<211> LENGTH: 65
<212> TYPE: DNA
<213> ORGANISM: Artificial Sequence
<220> FEATURE:
<223> OTHER INFORMATION: Primer

```
-continued

<400> SEQUENCE: 169
ggagccgccg ccaccggaac cgccgccgcc agatcctccg ccgcccttaa tttcaacctt      60
ggtgc                                                                 65

<210> SEQ ID NO 170
<211> LENGTH: 29
<212> TYPE: DNA
<213> ORGANISM: Artificial Sequence
<220> FEATURE:
<223> OTHER INFORMATION: Primer

<400> SEQUENCE: 170
ctcgaggaga cattgttatg acccagagc                                       29

<210> SEQ ID NO 171
<211> LENGTH: 27
<212> TYPE: DNA
<213> ORGANISM: Artificial Sequence
<220> FEATURE:
<223> OTHER INFORMATION: Primer

<400> SEQUENCE: 171
gggcccgctg gagacggtta caagggt                                         27

<210> SEQ ID NO 172
<211> LENGTH: 5
<212> TYPE: PRT
<213> ORGANISM: Artificial Sequence
<220> FEATURE:
<223> OTHER INFORMATION: Peptide

<400> SEQUENCE: 172

Met Ala Asp Tyr Lys
1               5
```

ANTIBODIES AGAINST PROSTATE-SPECIFIC STEM CELL ANTIGEN AND USE THEREOF

BACKGROUND OF THE INVENTION

The invention concerns recombinant antibodies binding to prostate-specific stem cell antigen (PSCA) and their use in diagnostics and therapy. The antibodies are suitable for use in the field of medicine, pharmacy and biomedical research.

Prostate carcinoma is one of the most frequent cancer-related causes of death in Germany. The standard therapy for a primary, organ-limited prostate carcinoma is currently radical prostatectomy, i.e. the complete removal of the prostate, seminal vesicles, and lymph nodes. An alternative to this is radiotherapy which is done by spiking the prostate with radioactive material (brachytherapy). Most patients with primary, local prostate carcinoma can be treated successfully by radical prostatectomy and radiotherapy. A relapse occurs in about 20-40% of the affected persons [Roehl 2004].

Presently, different antibody-based therapy procedures are being developed. In this context, it is of essential importance to identify target structures on the cancer cells which can serve as sites of attack for the antibody-based therapeutics. A suitable target structure as an attack site for the treatment of prostate cancer are surface proteins which are present primarily in the prostate tissue and which exhibit overexpression in malignant cells in comparison to healthy cells.

The prostate-specific stem cell antigen (PSCA) is such a surface molecule which is present specifically on prostate cells and is expressed at a higher rate in prostate carcinoma cells in comparison to healthy tissue (tumor-associated antigen). Human PSCA comprises 123 amino acids and has an N-terminal signal sequence, a C-terminal glycosylphosphatidylinositol (GPI) anchoring sequence and several N-glycosylation sites. PSCA is included in the Thy-1/Ly-6 family of the GPI-anchored cell surface molecules because, inter alia, it has the characteristic preserved cysteine residues of this family [Reiter 1998].

On account of the increased expression in prostate tumors, PSCA is a suitable target molecule for the therapy of prostate cancer and, up to now, different therapy strategies which are aimed at PSCA as a target have been developed. Evidence of the efficacy of PSCA as a therapeutic target in cancer therapy on human subjects has been produced, inter alia, by vaccination with dendritic cells which were loaded before with a PSCA peptide. Clinical studies (phase 1 and 2) with 12 hormone-refractory and chemotherapy-refractory prostate cancer patients have demonstrated that a vaccination with PSCA peptide-loaded dendritic cells caused a T-cell response against PSCA which correlated on average with an extended survival rate in five of the patients. In one patient even a reduction of the tumor mass was observed [Thomas-Kaskel 2006].

WO 2009/032949 A2 discloses monoclonal anti-PSCA antibodies (1G8) which are used for targeting tumors and for their detection. The CDR regions of the antibodies have the following amino acid sequences:

| | variable region of the light chain (1G8) | | variable region of the heavy chain (1G8) | |
|---|---|---|---|---|
| CDR1 | SASSSVRFIHW | SEQ ID No. 69 | DYYIHW | SEQ ID No. 72 |
| CDR2 | DTSKLAS | SEQ ID No. 70 | WIDPENGDTEFVPKFQG | SEQ ID No. 73 |
| CDR3 | QQWSSSPFT | SEQ ID No. 71 | TGGF | SEQ ID No. 74 |

On account of the cytotoxic properties of the 1G8 antibody, the latter is unsuited for targeting strategies which are based on the recruitment of effector cells (Gu 2005).

The antibodies disclosed in WO 2009/032949 A2 are used diagnostically preferably in the form of functional murine and humanized monoclonal antibodies as well as PSCA-specific minibodies and diabodies marked with radionuclides.

[Feldmann 2010] have developed bispecific recombinant antibodies with a PSCA-binding paratope and a CD3-binding paratope. The PSCA-binding paratope of the bispecific antibodies is derived from the PSCA antibody 7F5 [Morgenroth 2007] and comprises CDR regions with the following amino acid sequences:

| | variable region of the light chain (7F5) | | variable region of the heavy chain (7F5) | |
|---|---|---|---|---|
| CDR1 | RTSQDISNYLN | SEQ ID No. 27 | SYTMS | SEQ ID No. 30 |
| CDR2 | YTLKLNS | SEQ ID No. 28 | YIHNGGGHTYYPDTIKG | SEQ ID No. 31 |
| CDR3 | QQSKTLPWT | SEQ ID No. 29 | RMYYGNSHWYFDV | SEQ ID No. 32 |

The bispecific antibodies disclosed in [Feldmann 2010] in vitro successfully caused the specific T-cell mediated lysis of PSCA-positive tumor cells. For a specific lysis of about 40% of the employed PSCA-positive tumor cells, for a ratio of effector cells to PSCA-positive tumor cells of 20:1 at least 5 ng of the bispecific antibody disclosed in [Feldmann 2010] is to be used. In vitro, a specific lysis of maximally about 60% of the employed PSCA-positive tumor cells (in the presence of 50-100 ng of the antibody) has been achieved with the antibodies disclosed in [Feldmann 2010]. A further increase of the effectiveness could not be proved. Even in the presence of 1,000 ng of the bispecific antibody, a higher proportion of PSCA-positive tumor cells could not be lysed.

The known in vitro and in vivo data show that PSCA has a great potential as a target antigen for the immunotherapy of prostate carcinomas and is suitable as a diagnostic target.

The object of the invention is to provide improved antibodies against PSCA which are therapeutically effective in particular in the form of bispecific recombinant antibodies in low concentration and are able to lyse PSCA-positive tumor cells effectively.

SUMMARY OF THE INVENTION

The object is solved according to the invention by an antibody binding to prostate-specific stem cell antigen (PSCA) (herein also referred to as anti-PSCA antibody) which contains complementarity determining regions (CDR) with the following amino acid sequences:

CDR of the variable region of the light chain: CDR1 SEQ ID No. 1, CDR2 SEQ ID No. 2, CDR3 SEQ ID No. 3, and CDR of the variable region of the heavy chain: CDR1 SEQ ID No. 4, CDR2 SEQ ID No. 5, CDR3 SEQ ID No. 6.

The antibody according to the invention which is characterized by the aforementioned CDRs is also referred to herein simply as MB1. The inventors have unexpectedly found within the scope of extensive research that the antibody according to the invention in the form of recombinant bispecific antibodies can mediate even in very small quantities the specific lysis of PSCA-positive tumor cells. Further, it was found unexpectedly that the specific lysis of PSCA-positive tumor cells mediated by the new antibodies is more effective. Thus, in in vitro tests with bispecific antibodies containing an anti-PSCA antibody according to the invention, more than 90% of the employed PSCA-positive tumor cells were lysed. With the new anti-PSCA antibody the employed antibody amount can thus be reduced significantly. At the same time, the therapeutic efficacy is raised because with the antibody according to the invention PSCA-positive tumor cells can be more effectively lysed. On account of the low concentration with which an efficacy can be achieved with the antibody according to the invention, an improved killing of metastasized PSCA-positive cells is also possible with the antibody according to the invention. Comparative tests with prior art anti-PSCA 7F5 in a comparable bispecific construct clearly confirmed the superiority of the antibody according to the invention in in vitro (FIG. 3) as well as in vivo studies (FIG. 4).

Preferred anti-PSCA antibodies according to the invention contain CDR regions as defined above wherein the amino acid sequence of the variable regions of the light and heavy chain have amino acid sequence identity of at least 80%, preferably at least 90%, particularly preferred at least 95%, relative to the following amino acid sequence:

variable region of the light chain SEQ ID No. 24, variable region of the heavy chain SEQ ID No. 26, or variable region of the light chain SEQ ID No. 20, variable region of the heavy chain SEQ ID No. 22.

Of these, anti-PSCA antibodies with the CDR regions as defined above whose variable regions have a humanized structure are preferred. Particularly preferred are anti-PSCA antibodies whose variable region of the light chain contains the amino acid sequence according to SEQ ID No. 24 and whose variable region of the heavy chain contains the amino acid sequence according to SEQ ID No. 26.

The term "antibody" in the meaning of the invention encompasses all antibodies or antibody fragments which are able to bind specifically to an antigen. In case of recombinant antibodies, these are antibodies which are produced with the aid of genetically modified organisms. The term antibody encompasses the complete monoclonal antibodies as well as their epitope-binding fragments. In this context, the epitope-binding fragments (herein also referred to as antibody fragments) comprise those parts of the antibody which are able to bind to the antigen. Antibody fragments in the meaning of the invention encompass Fab, Fab', fa(ab')$_2$, Fd, single chains (single-chain) variable fragments (scFv), single chain antibodies, disulfide-linked variable fragments (sdFv), and fragments that contain either a variable region of the light chain ($V_L$) or a variable region of the heavy chain ($V_H$). Antibody fragments contain the variable regions either alone or in combination with other regions which are selected from the hinge region and the first, second, and third region of the constant region ($C_H1$, $C_H2$, $C_H3$).

Furthermore, the term antibody encompasses recombinant antibodies, like diabodies, triabodies, and tetrabodies. Also encompassed by the term antibody are chimeric antibodies in which different parts of the antibody originate from different species, for example, antibodies with a murine variable region which is combined with a human constant region. Humanized antibodies are also encompassed by the term antibody. The goal of humanization of antibodies is the reduction of the immunogenicity of a xenogeneic antibody, for example murine antibodies, for use in the human system wherein the full binding affinity and the antigen specificity are preserved. Humanized antibodies can be produced by different known ways, for example, by resurfacing and CDR grafting. In resurfacing, all non-CDR regions on the surface of the antibody are modified by a combination of molecular modelling, statistical analyses, and mutagenesis so that they resemble the surface of antibodies of the target organism. With CDR grafting the CDR regions of the antibody to be humanized are introduced into human variable regions.

Antibody fragments are linked together if necessary by a linker. The linker comprises a short peptide sequence (preferably with a length of 10 to 50 amino acid residues) which is selected such that the antibody fragment has such a three-dimensional folding structure of the $V_L$ and $V_H$ that it has the antigen specificity of the complete antibody. Glycine serine linkers or linker peptides with an amino acid sequence according to SEQ ID No. 75 or SEQ ID No. 76 are preferred.

The term "variable region" means herein the parts of the heavy and light chains of the antibodies which differ between antibodies in their sequence and determine the specificity of the antibody and binding to its antigen. In this context, the variability is not distributed evenly in the variable region but is usually concentrated within three defined segments of the variable region, the complementarity determining regions (CDRs, also referred to as hypervariable regions) which are contained in the variable regions of the light chain as well as the heavy chain. The antigen binding site of an antibody, the so-called paratope, is characterized by the hypervariable regions (CDR) of the light and heavy chains of the antibody.

For describing antibodies the simplified name anti-"antigen" antibody is also used herein to show that this is an antibody which binds specifically to the antigen defined in the name. For example, an "anti-PSCA" antibody in the meaning of the invention is to be understood as an antibody which binds specifically to the antigen PSCA. A specific binding of an antibody to a specific antigen is to be understood herein such that an antibody with a high affinity binds to the specific antigen and binds with a distinctly lower affinity, and preferably does not bind, to other antigens.

Preferred antibodies are present in the form of a scFv fragment or a F(ab')$_2$ fragment. Further preferred antibodies are bispecific antibodies which are produced recombinantly and which contain two different paratopes with one directed against PSCA and the other not directed against PSCA. The other paratope of the bispecific antibody is preferably directed against a surface structure on an effector cell or against a peptide of a length of 10 to 50 amino acids (preferably a sequence of the human La protein of a length of 10 to 50 amino acids, particularly preferred against a peptide with one of the amino acid sequences according to SEQ ID No. 75 or SEQ ID No. 76).

Anti-PSCA antibodies according to the invention (naive or recombinant antibodies) with a conjugated effector group are preferred. Conjugation means, in this context, coupling of a substance, here the effector group, to the antibody. The bond of the antibody with the effector group is produced preferably by recombinant expression in the form of a fusion protein or by in vitro methods wherein the effector group is preferably bonded by chemical linker groups to the antibody (for example, by thioether bonds or disulfide bonds). They can be bonded to the antibody also by an intermediary carrier molecule, for example, serum albumin. If necessary, an antibody according to the invention contains several effector groups. In this context, effector groups are preferably selected from active ingredients, peptides (with a length of 10 to 100 amino acids), proteins (with a length of more than 100 amino acids), co-stimulating molecules, dyes or contrast media.

Preferred anti-PSCA antibodies according to the invention are conjugated with active ingredients, i.e., with pharmaceutically effective substances. Preferred active ingredients encompass toxins, preferably cytostatic agents; of these, preferably selected are: maytansinoids and maytansinoid analogs, taxoids, CC-1065 and CC-1065 analogs, dolastatin and dolastatin analogs, methotrexate, daunorubicin, doxorubicin, vincristine, vinblastin, melphalan, mitomycin C, chlorambucil and calicheamicin.

Further preferred anti-PSCA antibodies according to the invention are conjugated with contrast media. Preferred contrast media are radionuclides; of these, preferred are the radioactive isotopes of technetium, rhenium, yttrium, copper, gallium, indium, bismuth and platinum, in particular $^{99m}$Tc, $^{90}$Y, $^{186}$Re, $^{188}$Re, $^{68}$Ga, and $^{111}$In.

Further preferred anti-PSCA antibodies according to the invention are conjugated with a protein, preferably an enzyme, preferably an enzyme suitable for the ADEPT system, a co-stimulating molecule, preferably toll-like receptor ligand, of these preferably CpG, or with a nucleic acid.

Further preferred anti-PSCA antibodies according to the invention are conjugated with a dye, preferably a fluorescent dye.

Further preferred antibodies according to the invention are conjugated with a peptide which contains a binding region to which an antibody specific for the peptide binds specifically. Preferably, the peptide comprises a peptide sequence of a length of 10 to 50 amino acids of an alpha-helical region of the human La protein (the amino acid sequence of the human La protein corresponds to SEQ ID No. 77). Particularly preferred are peptides with an amino acid sequence identity of at least 90%, preferably at least 95%, particularly preferred at least 99%, relative to one of the amino acid sequences according to SEQ ID No. 75 or SEQ ID No. 76.

It is particularly preferred to produce anti-PSCA antibodies according to the invention by recombination. Preferably, recombinant anti-PSCA antibodies according to the invention contain at least two different binding units, wherein
  at least one of the binding units specifically binds to PSCA and contains the paratope of the anti-PSCA antibody according to the invention, and
  at least one other one of the binding units binds specifically to an antigen other than PSCA, preferably to a surface structure on an effector cell.

The PSCA-binding binding unit comprises therefore an anti-PSCA antibody according to the invention and contains therefore at least the following CDR regions:
  CDR of the variable region of the light chain comprising the following amino acid sequences: CDR1 SEQ ID No. 1, CDR2 SEQ ID No. 2, CDR3 SEQ ID No. 3, and
  CDR of the variable region of the heavy chain comprising the following, amino acid sequences: CDR1 SEQ ID No. 4, CDR2 SEQ ID No. 5, CDR3 SEQ ID No. 6

The term "binding unit" in the meaning of the invention refers to any molecular structure which specifically binds defined substances or structures. Depending on the substance or structure to be bonded, the binding unit has different structures. Hence, the term "binding unit" in the meaning of the invention encompasses therefore antibodies (in this case the binding unit contains at least the functional paratope of the antibody) as well as other molecules, preferably proteins which form a specific binding with an antigen. Such molecules are preferably ligands which bind specifically to a surface structure (for example, a surface receptor) on a cell, in particular on an effector cell.

Preferred binding units which are included in antibodies according to the invention bind specifically to an effector cell. The definition of effector cells in the meaning of the invention encompasses all cells of the native and adaptive immune system which provide immune responses or are involved actively therein. Preferably, the effector cell is selected from T lymphocytes, NK cells, monocytes, macrophages, dendritic cells, and granulocytes. Particularly preferred are binding units which bind against surface structures on T lymphocytes.

When a recombinant antibody according to the invention contains at least two different antibodies (at least one anti-PSCA antibody according to the invention and at least one other antibody which does not bind specifically to PSCA), it is preferably in the form of a diabody, triabody or tetrabody. Preferred are bispecific antibodies from single chain antibodies (single chain bispecific diabody, scBsDb) or bispecific tandem antibodies from single chain antibodies (single chain bispecific tandem antibody, scBsTaFv). It is particularly preferred that a recombinant antibody according to the invention is present in the form of an scBsTaFv.

Preferred antibodies that do not bind to PSCA-binding antibodies which are contained in a recombinant antibody according to the invention (in this case the recombinant antibody is a bispecific antibody) are antibodies which bind specifically to a surface structure of an effector cell. In this case the binding unit that does not bind to PSCA contains at least the paratope of the antibody which binds to a surface structure of an effector cell. It is particularly preferred that the antibodies are directed against the following surface structures on effector cells: CD3, CD8, CD4, CD25, CD28, CD16, NKG2D, NKp46, NKp44, activating KIR receptors (activating killer cell immunoglobulin-like receptors). Particularly preferred are antibodies which are directed against CD3 (anti-CD3 antibody), wherein the anti-CD3 antibody contains CDR regions with the following amino acid sequences:
  CDR of the variable region of the heavy chain: CDR1 SEQ ID No. 66, CDR2 SEQ ID No. 67, CDR3 SEQ ID No. 68, and
  CDR of the variable region of the light chain: CDR1 SEQ ID No. 58, CDR2 SEQ ID No. 59, CDR3 SEQ ID No. 60.

Further preferred are recombinant anti-PSCA antibodies which contain at least two different binding units wherein at least one other one of the binding units is a ligand (preferably a protein or a glycan) which binds specifically to a surface structure on an effector cell. Preferred ligands influence the activity of the effector cells by their binding to the (effector) cell surface. In this context, the ligand is selected such that that it binds specifically to surface structures of effector cells and, by the binding action, triggers signal cascades for activation of the effector cells. Preferred as a ligand is a protein structure or a glycan which binds specifically to a receptor which is expressed specifically on the surface of effector cells, wherein the ligand causes, due to its binding action, at the receptors an activation of the effector cell. It is particularly preferred that the protein structures are selected from ULB-Ps (e.g. ULB-P2), MICA, MICB, and cytokines (for example IL2 and IL15).

Antibodies according to the invention, in particular recombinant antibodies according to the invention, are suited for specifically binding to PSCA-positive cells in vivo and in vitro. Hence, the invention also encompasses the use of the anti-PSCA antibodies according to the invention as a medicament, in particular for the treatment of tumor diseases, prostate cancer, or as a diagnostic agent.

The invention encompasses further the antibodies according to the invention for the therapy of tumor diseases, in particular prostate cancer. The invention also encompasses the use of the antibodies according to the invention for producing a medicament for the treatment of tumor diseases, in particular prostate cancer.

A preferred therapeutic use of the (preferably recombinant) antibodies according to the invention is the treatment of tumor diseases, preferably prostate cancer. In the therapeutic application, the antibodies according to the invention are employed preferably for targeting the tumor tissue with therapeutically effective substances or effector cells. For targeting the tumor tissue with therapeutically effective substances, recombinant antibodies according to the invention which are conjugated with an active ingredient are used preferably. For targeting the tumor tissue with effector cells, recombinant antibodies according to the invention which contain at least two different binding units are used preferably, wherein at least one of the binding units is an anti-PSCA antibody according to the invention and another one of the binding units binds specifically to an effector cell, preferably to CD3 on T cells. The above mentioned antibodies are used preferably for this purpose.

A pharmaceutical composition which contains an antibody according to the invention in association with a pharmaceutically acceptable thinner or carrier is also encompassed by the invention. Preferably, the pharmaceutical composition according to the invention is administered in a form suitable for intravenous administration.

Preferably, the antibodies are present in the pharmaceutical composition according to the invention in recombinant form as chimeric or, particularly preferred, humanized antibodies which have a reduced immunogenity.

The pharmaceutical compositions according to the inventions encompass various dosage forms and are preferably suitable for parenteral, particularly preferred for intravenous, administration. Preferably, the parenteral pharmaceutical composition is present in an administration form which is suitable for injection. Hence, particularly preferred pharmaceutical compositions are solutions, emulsions or suspensions of the antibody in a pharmaceutically acceptable thinner or carrier.

Pharmaceutically acceptable carriers are preferably sterile liquids, in particular water, buffered water, 0.4% saline solution, 0.3% glycine and the like. The pharmaceutical compositions are sterilized by customary, well known technologies. The compositions contain preferably pharmaceutically acceptable excipients such as those that are required in order to provide approximately physiological conditions and/or to increase the stability of the antibodies contained in the composition such as agents for adjusting the pH value and buffering agents, agents for adjusting toxicity and the like, preferably selected from sodium acetate, sodium chloride, potassium chloride, calcium chloride, and sodium lactate.

The pharmaceutical composition is preferably an injectable buffered solution which contains between 0.1 to 500 mg/ml antibodies, particularly preferred between 0.1 to 250 mg/ml antibodies, in particular together with 1 to 500 mmol/l of a buffering agent. The injectable solution is present preferably in a liquid or lyophilized dosage form. The buffering agent is selected preferably from histidine, sodium succinate, sodium citrate, sodium phosphate and potassium phosphate.

Preferably, a pharmaceutical composition according to the invention contains at least two different (preferably recombinant) antibodies, wherein at least one anti-PSCA antibody according to the invention is contained and at least one other recombinant antibody which forms a specific bond with the anti-PSCA antibody according to the invention. Particularly preferred are the following combinations:
 a) a recombinant anti-PSCA antibody which is conjugated with a peptide having a length of 10 to 50 amino acids and another recombinant antibody which binds specifically to the peptide, or
 b) a bispecific anti-PSCA antibody which contains, in addition, an antibody which binds to a peptide having a length of 10 to 50 amino acids and another recombinant antibody which binds against an antigen other than PSCA and which contains a peptide to which the bispecific anti-PSCA antibody binds.

The at least two different antibodies are present preferably separately packaged in the pharmaceutical composition according to the invention.

A preferred pharmaceutical composition which contains the combination defined under a) comprises:
 a recombinant anti-PSCA antibody which is conjugated with a peptide which contains an amino acid sequence, having a length of 10 to 50 amino acids, of an alpha-helical region of the human La protein (the amino acid sequence of the human La protein corresponds to SEQ ID No. 77). Preferably, the anti-PSCA antibody is conjugated with a peptide with an amino acid sequence identity of at least 90%, preferred at least 95%, particularly preferred at least 99%, relative to one of the amino acid sequences according to SEQ ID No. 75 or SEQ ID No. 76.
 A further (preferably recombinant) antibody which contains a paratope which binds specifically against the peptide of the anti-PSCA antibody and which contains another binding unit which binds specifically to a surface structure of an effector cell. Preferred binding units thereof correspond to the ones defined above. In case that the recombinant anti-PSCA antibody is conjugated with a peptide with an amino acid-sequence identity of at least 90%, preferred at least 95%, particularly preferred at least 99%, relative to one of the amino acid sequences according to SEQ ID No. 75 or SEQ ID No. 76, the other recombinant antibody contains preferably the following amino acid sequences as a paratope which binds to the peptide:
  CDR of the variable region of the light chain: CDR1 SEQ ID No. 78, CDR2 SEQ ID No. 79, CDR3 SEQ ID No. 80, and CDR of the variable region of the heavy chain: CDR1 SEQ ID No. 81, CDR2 SEQ ID No. 82, CDR3 SEQ ID No. 83 (referred to herein also as "5B9" paratope), or
  CDR of the variable region of the light chain: CDR1 SEQ ID No. 84, CDR2 SEQ ID No. 85, CDR3 SEQ ID No. 86, and CDR of the variable region of the heavy chain: CDR1 SEQ ID No. 87, CDR2 SEQ ID No. 88, CDR3 SEQ ID No. 89 (herein also referred to as "7B6" paratope).

Preferred combinations thereof are
 an anti-PSCA antibody that contains a peptide with an amino acid sequence identity of at least 90%, preferred at least 95%, particularly preferred at least 99%, relative to one of the amino acid sequences according to SEQ ID No. 75 with another antibody which contains the 5B9 paratope, or an anti-PSCA antibody that contains a peptide with an amino acid sequence identity of at least 90%, preferred at least 95%, particularly preferred at least 99%, relative to one of the amino acid sequences according to SEQ ID No. 76 with another antibody which contains this 7B6 paratope.

A preferred pharmaceutical composition which contains the combination defined under b) comprises:

Another antibody which binds specifically to a surface structure of an effector cell and contains an amino acid sequence, having a length of 10 to 50 amino acids, of an alpha-helical region of the human La protein, preferably a peptide with an amino acid sequence identity of at least 90%, preferred at least 95%, particularly preferred at least 99%, relative to one of the amino acid sequences according to SEQ ID No. 75 or SEQ ID No. 76.

A bispecific anti-PSCA antibody which is conjugated with an antibody which specifically binds the amino acid sequence, having a length of 10 to 50 amino acids, of an alpha-helical region of the human La protein. In case that the other recombinant antibody contains a peptide with an amino acid sequence identity of at least 90%, preferred at least 95%, particularly preferred at least 99%, relative to one of the amino acid sequences according to SEQ ID No. 75 or SEQ ID No. 76, the bispecific anti-PSCA antibody preferably contains a 5B9 paratope or 7B6 paratope as defined above.

Preferred combinations thereof are a bispecific anti-PSCA antibody containing the 5B9 paratope and another recombinant antibody that contains a peptide with an amino acid sequence identity of at least 90%, preferred at least 95%, particularly preferred at least 99%, relative to one of the amino acid sequences according to SEQ ID No. 75, or a bispecific anti-PSCA antibody containing the 7B6 paratope and another recombinant antibody that contains a peptide with an amino acid sequence identity of at least 90%, preferred at least 95%, particularly preferably at least 99%, relative to one of the amino acid sequences according to SEQ ID No. 76.

A preferred diagnostic use is in vivo diagnostics wherein an anti-PSCA antibody according to the invention conjugated with contrast medium is used for the targeted transport of contrast media to the tumor tissue. A further preferred diagnostic use of the anti-PSCA antibodies according to the invention is in vitro diagnostics wherein preferably an anti-PSCA antibody according to the invention conjugated with a dye is used for detection of PSCA-positive cells in a sample, especially in a tissue sample.

The invention also encompasses a diagnostic composition which contains an anti-PSCA antibody according to the invention. The anti-PSCA antibody is present therein preferably in a buffered solution, preferably in buffered saline solution.

The invention also encompasses a nucleic acid whose nucleotide sequence codes for an anti-PSCA antibody according to the invention. Preferably, the segments that code for the CDR of the variable regions of the light and heavy chain contain the following nucleotide sequences:

CDR of the variable region of the light chain: CDR1 SEQ ID No. 7, CDR2 SEQ ID No. 9, CDR3 SEQ ID No. 11, and CDR of the variable region of the heavy chain: CDR1 SEQ ID No. 13, CDR2 SEQ ID No. 15, CDR3 SEQ ID No. 17, or CDR of the variable region of the light chain: CDR1 SEQ ID No. 8, CDR2 SEQ ID No. 10, CDR3 SEQ ID No. 12, and CDR of the variable region of the heavy chain: CDR1 SEQ ID No. 14, CDR2 SEQ ID No. 16, CDR3 SEQ ID No. 18.

The term "nucleic acids" in the meaning of the invention encompasses in addition to deoxyribonucleic acid (DNA) and ribonucleic acids (RNA) also all the other linear polymers in which the bases adenine (A), cytosine (C), guanine (G), and thymine (T) or uracil (U) are arranged in a suitable sequence (nucleic acid sequence). The invention thus also encompasses the corresponding RNA sequences (in which thymine is replaced with uracil), complementary sequences, and sequences with modified nucleic acid backbone or 3' or 5' terminus. In this context, the term "nucleic acid sequences with modified backbone" encompasses all other linear polymers in which the bases adenine (A), cytosine (C), guanine (G), and thymine (T) or uracil (U) are arranged in suitable sequence, such as e.g. sequences with phosphothioate, phosphoamidate or O-methyl-derivatized backbone, peptide nucleic acids (PNA), and locked nucleic acids (LNA), or mixed backbone. In this context, the term "modified 3' or terminus" encompasses modifications which serve for stabilization as well as binding of markers. Examples of marker are enzymes, dyes or fluorescent dyes, radionucleotides, as well as haptenes, as e.g. digoxigenin or biotin.

The invention also encompasses a vector (also: "expression vector") which contains a nucleic acid according to the invention. In the meaning of the invention, an expression vector is understood as a plasmid, virus or other carrier containing a nucleic acid sequence according to the invention by recombination through insertion or incorporation. The expression vector contains typically a replication starting point, a promoter, as well as specific gene sequences which allow a phenotype selection of host cells containing the expression vector.

The invention encompasses further a host cell or a non-human host organism containing a nucleotide sequence according to the invention or a vector according to the invention. In this context, the nucleotide sequence or the vector are contained recombinantly in the host cell or the non-human host organism.

A host cell in the meaning of the invention is a naturally occurring cell or a transformed or genetically modified cell line which contains at least one vector according to the invention. The invention encompasses in this context transient transfectants (e.g., by mRNA injection) or host cells in which at least one expression vector according to the invention is included as a plasmid or artificial chromosome, as well as host cells in which an expression vector according to the invention is integrated stably into the genome of the host.

The host cell is selected preferably from cells of prokaryotes and eukaryotes. Human embryonic stem cells which were obtained by destroying embryos are no host cells in the meaning of the invention. Preferred prokaryote cells are selected from cells of *Escherichia coli* and *Bacillus subtilis*. Preferred eukaryote cells are selected from yeast cells (preferably *Saccharomyces cerevisiae* or *Pichia pastoris*), insect cells, amphibious cells and mammalian cells (preferably CHO, HeLa, HEK293).

Non-human host organisms contain a vector according to the invention which is integrated stably into the genome of the host organism or individual cells of the host organism. Preferred host organisms are plants, invertebrates or vertebrates, in particular *Bovidae, Drosophila melanogaster, Caenorhabditis elegans, Xenopus laevis*, medaka, zebra fish or *Mus musculus*, or cells or embryos of the named organisms.

The invention provides anti-PSCA antibodies and corresponding expression systems with which human PSCA can be bound more effectively. In this way, the anti-PSCA antibody according to the invention is suitable particularly for the application in therapy systems with which killing of tumor cells can be mediated by recruitment of effector cells. On account of the higher affinity of the antibodies according to the invention to PSCA, a substantially smaller quantity of antibodies is necessary for binding (for example, in therapeutic use). It has been demonstrated that the anti-PSCA antibody according to the invention can mediate the specific lysis of PSCA-positive tumor cells in clearly lower concentrations and with clearly higher efficiency. This has, on the one hand, cost advantages because the antibody consumption can be reduced. On the other hand, in the therapeutic use an improved targeting primarily also of metastasized cells is to be expected as well as fewer side effects due to lower administration quantities.

BRIEF DESCRIPTION OF THE DRAWINGS

The invention will be explained in more detail with the aid of the following figures and embodiments without limiting the invention to them.

FIG. 1 Schematic illustration of different recombinant antibodies according to the invention. A) Bispecific antibody in form of an scBsTaFv containing a binding unit against PSCA and a binding unit against CD3. B) Recombinant antibody according to the invention against PSCA containing a peptide tag (5B9), for use with the also shown bispecific antibody in form of an scBsTaFv containing a binding unit against CD3 and a binding unit against the 5B9 region of the human La protein. C) Recombinant antibody according to the invention against PSCA containing a peptide tag (7B6), for use with the also shown bispecific antibody in the form of an scBsTaFv containing a binding unit against CD3 and a binding unit against the 7B6 region of the human La protein. The respective $V_H$ and $V_L$ subunits are linked by the linker peptides with the amino acid sequences shown in the Figures.

PREFERRED EMBODIMENTS

Example 1

Figure 2:
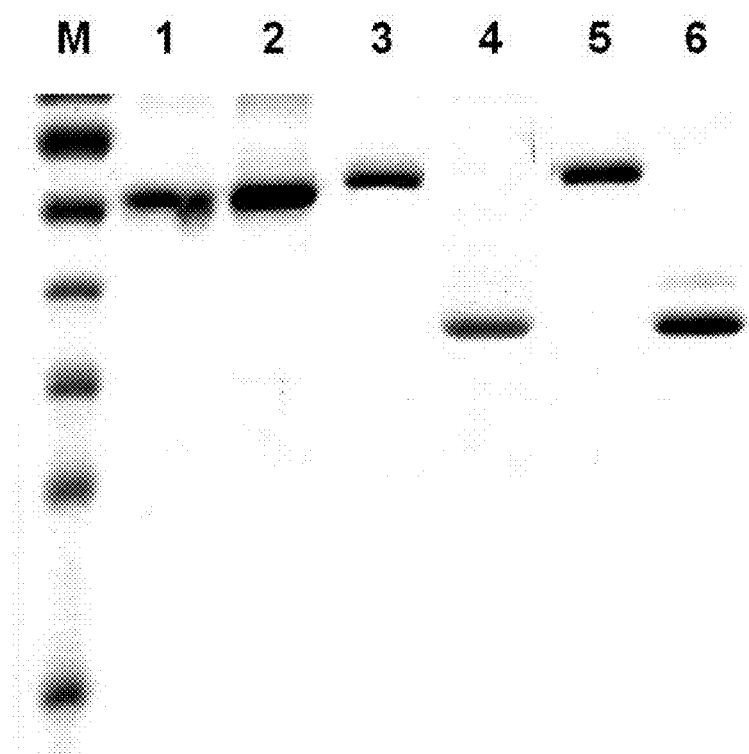
FIG. 2 SDS PAGE of recombinant antibodies. Lane 1: bispecific humanized antibody CD3-7B6 (scBsTaFv CD3-7B6); lane 2: bispecific humanized antibodies CD3-5B9 (scBsTaFv CD3($G_4$S)-5B9); lane 3: bispecific murine antibody CD3-PSCA(7F5) according to the invention (scBsTaFv CD3-PSCA(7F5)); lane 4: monospecific humanized antibody scFv PSCA(MB1)-7B6 according to the invention; lane 5: bispecific humanized antibodies CD3-PSCA(MB1) (scBsTaFv CD3-PSCA(MB1)); lane 6: monospecific humanized antibody scFv PSCA(MB1)-5B9 according to the invention. M . . . marker with fragment sizes (from top to bottom): 70 kDa, 55 kDa, 40 kDa, 35 kDa, 25 kDa, 15 kDa.

Preparation of Bispecific Recombinant Antibodies (scBsTaFv) which Bind Specifically to PSCA (Direct Targeting)

Figure 1:
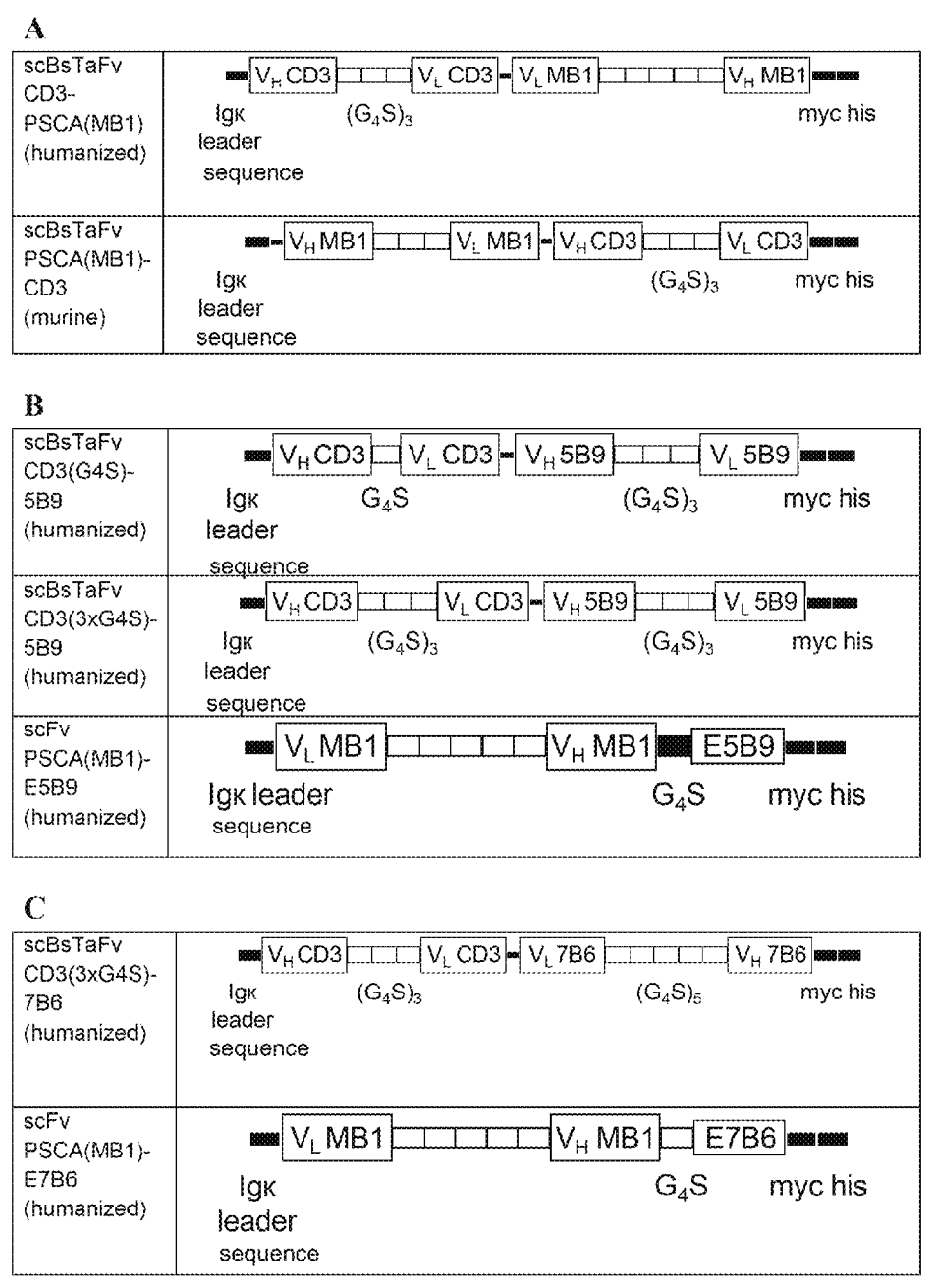

For use in targeting PSCA$^+$ cells, a bispecific antibody (single chain bispecific diabody, scBsTaFv) was prepared which binds with one binding unit to PSCA and with the other binding unit to CD3. The bispecific antibody is called herein also simply CD3-PSCA(MB1) and is schematically shown in FIG. 1A.

The PSCA-binding domain contains the variable region of the anti-PSCA MB1 antibody according to the invention (murine anti-PSCA antibody: heavy chain SEQ ID No. 22, light chain SEQ ID No. 20; humanized anti-PSCA antibody: heavy chain SEQ ID No. 26, light chain SEQ ID No. 24). It serves for binding to the PSCA-positive tumor cells. The other domain binds to CD3, a component of T cell receptor complex, and serves for activation of T cells. This enables the recruitment of T of cells to the PSCA-positive cells and mediates in this manner the specific lysis of the PSCA-positive cells by the T cells.

For the generation of the monoclonal anti-PSCA MB1 antibodies, H-2d positive C3Hx Balb/C F1 mice were immunized with P815 cells, the PSCA recombinantly expressed on the surface. By fusion of spleen cells and myeloma cells, hybridoma cells were generated that secrete monoclonal anti-PSCA antibodies. After single cloning of these hybridoma cells, it was possible to select the clone MB1. For generating recombinant anti-PSCA MB1 antibodies the nucleic acid sequences of the variable domain of the heavy ($V_H$) and light ($V_L$) antibody chain were identified. For this purpose, first mRNA was isolated from the hybridoma cells secreting anti-PSCA MB1 and transcribed to cDNA. Afterwards the variable domain of the heavy chain of the isotype IgG1 was amplified with degenerated primers (primer pair SEQ ID No. 90 and 91) as well as the variable domain light κ chain with the aid of degenerated primers (primer pair SEQ ID No. 92 and 93). The PCR products were subcloned in the vector pGEM T-easy and sequenced.

For cloning the murine single chain fragments (scFv) of the anti-PSCA MB1 antibody (herein simply referred to as "scFv MB1"), in which the variable region of the heavy chain is linked by three glycine-serine linkers ($G_4$S, SEQ ID No. 131) with the variable region of the light chain, the nucleic acid sequence of the variable region of the heavy chain of the anti-PSCA MB1 antibody was amplified with the aid of the primer pair according to SEQ ID No. 94 and 95. The nucleic acid sequence of the variable region of the light chain of the anti-PSCA MB1 antibody was amplified with the aid of the primer pair according to SEQ ID No. 96 and 97. The amplified nucleic acids were fused by means of overlap PCR to scFv PSCA MB1 and were cloned via SfiI and NotI in the eukaryotic expression vector pSecTag2B (the expression vector is referred to herein also as "pSecTag2B_scFv MB1 murine").

For cloning the bispecific tandem antibody (scBsTaFv) which is directed against PSCA and CD3 and which contains the CDR regions of the murine MB1 antibody, the nucleic acid sequence of a murine anti-CD3 scFv was amplified with a primer pair according to SEQ ID No. 98 and 99 and via or ApaI 3′-terminally cloned from the murine scFv MB1 into the previously produced expression vector "pSecTag2B_scFv MB1 murine" so that the vector "pSecTag2B_scBsTaFv PSCA (MB1)-CD3 murine" was generated.

For cloning the bispecific tandem antibody (scBsTaFv) which is directed against PSCA and CD3 and which contains the CDR regions of the humanized MB1 antibody, the framework regions (FWR) of the PSCA MB1 and CD3 antibodies were humanized. For this purpose, the FWR of the variable murine antibody domains were replaced with the human FWR sequences of highly homologous human IgG1. In addition, the humanized antibody sequences were optimized concerning their expression and secretion by human cell lines. For the humanization of the murine scFv CD3 or scFv MB1 first the humanized $V_H$ and $V_L$ sequences were amplified individually as described above and were joined afterwards by PCR. The humanization of the $V_H$ or $V_L$ sequence occurred through the agglomeration of overlapping oligonucleotides and subsequent amplification of the humanized $V_H$ or $V_L$ nucleic acid sequence. In order to be able to ascertain the sequences of the overlapping oligonucleotides, first the murine $V_H$ or $V_L$ sequence was compared against a human IgG database (NCBI IgBlast), the human IgG which provided the greatest homology was identified, and then finally the humanized $V_H$ or $V_L$ sequence was theoretically created, and the overlapping oligonucleotides synthesized. Different bispecific antibodies were constructed in which linker peptides of different length were used.

Humanization of the Anti-CD3 Antibody

For the humanization of the variable region of the heavy chain of the anti-CD3 antibody, oligonucleotides according to SEQ ID No. 100 to 105 were agglomerated. Afterwards the humanized nucleic acid sequence of the variable region of the heavy chain of the anti-CD3 antibody (with a $G_4S$ linker peptide, SEQ ID No. 132) was amplified with the aid of the primer pair according to SEQ ID No 105 and 106. For the humanization of the variable region of the light chain of the anti-CD3 antibody, oligonucleotides according to SEQ ID No. 107 to 112 were agglomerated. The humanized nucleic acid sequence of the variable region of the light chain of the anti-CD3 antibody was amplified with the primer pair according to SEQ ID No. 112 and 113.

For generating the humanized scFv of the anti-CD3 antibody in which the variable region of the heavy chain is linked by one glycine-serine linker ($G_4S$) with the variable region of the light chain, the humanized nucleic acid sequence of the variable region of the heavy chain of the anti-CD3 antibody was first cloned via SfiI and BamHI into the expression vector pSecTag2B and afterwards via. BamHI and NotI the humanized nucleic acid sequence of the variable region of the light chain of the anti-CD3 antibody was inserted downstream thereof into the same expression vector.

For generating the humanized scFv of the anti-CD3 antibody in which the variable region of the heavy chain is linked by three glycine-serine linkers ($G_4S$) with the variable region of the light chain, the humanized nucleic acid sequence of the variable region of the heavy chain of the anti-CD3 antibody was prepared with three glycine-serine linkers ($G_4S$). For this purpose, the humanized nucleic acid sequence of the variable region of the heavy chain of the anti-CD3 antibody (with three $G_4S$ linker peptides) was amplified with the aid of the primer pair according to SEQ ID No. 105 and 114 and via SfiI and BamHI cloned into the expression vector pSecTag2B and afterwards via BamHI and NotI the humanized nucleic acid sequence of the variable region of the light chain of the anti-CD3 antibody was inserted downstream thereof into the same expression vector.

Humanization of the Anti-PSCA MB1 Antibody

For the humanization of the variable region of the light chain of the anti-PSCA MB1 antibody, oligonucleotides according to SEQ ID No. 115 to 118 were agglomerated. The humanized nucleic acid sequence of the variable region of the light chain of the anti-PSCA MB1 antibody was amplified with the primer pair according to SEQ ID No. 119 and 120.

For humanization of the variable region of the heavy chain of the anti-PSCA MB1 antibody, oligonucleotides according to SEQ ID No. 121 to 125 were agglomerated. The humanized nucleic acid sequence of the variable region of the heavy chain of the anti-PSCA MB1 antibody was amplified with the primer pair according to SEQ ID No. 126 and 127.

Preparation of the Bispecific Humanized Antibody scBsTaFv CD3-PSCA(MB1)

Finally, the humanized nucleic acid sequences of the variable region of the heavy chain and the variable region of the light chain of the MB1 antibody were agglomerated and amplified by means of overlap PCR using the primers according to SEQ ID No. 128 and 129. The so generated nucleic acid sequence coding for the humanized scFv MB1 (in the organization $V_L$-$G_4SG_4SGASAAG_4SG_4S$-$V_H$, linker peptide according to SEQ ID No. 130) was cloned via XhoI and ApaI downstream from the afore described humanized scFv of the anti-CD3 antibody (with three $G_4S$ linker peptides) whereby the expression vector "pSecTag2B_scBsTaFv PSCA(MB1)-CD3 human" was generated.

For expressing the bispecific humanized antibody according to FIG. 1 A, Hek293T cells were transfected with the expression vector and the secreted antibodies were purified from the cell culture supernatant by means of nickel-affinity chromatography, if necessary in combination with a fractionated ammonium sulfate precipitation. FIG. 2, lane 5, shows SDS gel electrophoresis image of the purified bispecific antibody.

Example 2

Preparation of Bispecific Recombinant Antibodies which Bind Specifically to PSCA (Modular Targeting)

For providing a pharmaceutical composition according to the invention ("modular targeting system 1", schematically shown in FIG. 1B), the following recombinant antibodies were produced:
  recombinant anti-PSCA antibody according to the invention containing a peptide according to SEQ ID No. 75 (herein also "E5B9"). This antibody is named in the following scFv PSCA(MB1)-E5B9.
  bispecific antibody (scBsTaFv) directed against CD3 and the peptide according to SEQ ID No. 75. The paratope directed against CD3 comprises the following amino acid sequences of the variable regions: heavy chain SEQ ID No. 65, light chain SEQ ID No. 57. The paratope directed against the peptide according to SEQ ID No. 75 comprises the following amino acid sequences of the hypervariable regions of the variable regions: light chain CDR1 SEQ ID No. 78, CDR2 SEQ ID No. 79, CDR3 SEQ ID No. 80, heavy chain CDR1 SEQ ID No. 81, CDR2 SEQ ID No. 82, CDR3 SEQ ID No 83. This antibody is named in the following scBsTaFv CD3-5B9.

Two different scBsTaFv CD3-5B9 were prepared which merely differ relative to each other in the linker peptide between VH and VL of the anti-CD3 antibody (see FIG. 1B).

Cloning of the Humanized scFv PSCA(MB1)-E5B9:

For generating the humanized scFv PSCA(MB1) with E5B9 epitope at the C terminus (MB1 [$V_L$-$G_4SG_4SGASAAG_4SG_4S$-MB1 VH]-[$G_4S$-E5B9], shown in FIG. 1B at the bottom), the humanized scFv PSCA (MB1 ($V_L$-$G_4SG_4SGASAAG_4SG_4S$-MB1 MB1 $V_H$-$G_4S$, linker peptide according to SEQ ID No. 130 and 132) described in example 1 was amplified by means of the primers according to SEQ ID No. 134 and 135 and afterwards via SfiI and NotI cloned in pSecTag2B. After agglomeration of the oligonucleotides according to SEQ ID No. 136 and 137, the nucleic acid sequence for E5B9 was cloned via NotI and XhoI at the 3' end of the humanized scFv PSCA (MB1), whereby the construct "pSecTag2B_scFv PSCA (MB1)-E5B9 humanized" was generated.

Cloning of Two Effector Modules "scBsTaFv CD3 (G4S)-5B9" and "scBsTaFv CD3 ($3\times G_4S$)-5B9" that are Binding to T Cells and to the E5B9 Peptide As schematically shown in FIG. 1B, for building the modular targeting system I comprising scFv PSCA(MB1)-5B9 two so-called effector modules (bispecific antibodies scBsTaFv CD3-5B9) were produced which differ in the number of the glycine-serine ($G_4S$) elements of the linker peptide between the $V_H$ and $V_L$ chains of the anti-CD3 domain and therefore were named "scBsTaFv CD3(G4S)-5B9" or, "scBsTaFv CD3 ($3\times G_4S$)-5B9".

Cloning of "scBsTaFv CD3(G4S)-5B9" Humanized (See Schematic FIG. 1B at the Top):

For the humanization of the variable region of the heavy chain of the 5B9 antibody (specifically directed against the peptide E5B9), oligonucleotides according to SEQ ID No. 138 to 142 were agglomerated. Afterwards the humanized nucleic acid sequence of the variable region of the heavy chain of the 5B9 antibody (with a $G_4S$ linker peptide, SEQ ID No. 132) was amplified with the aid of the primer pair according to SEQ ID No. 143 and 144. For the humanization of the variable region of the light chain of the 5B9 antibody oligonucleotides according to SEQ ID No. 145 to 149 were agglomerated. The humanized nucleic acid sequence of the variable region of the light chain of the 5B9 antibody was amplified with the primer pair according to SEQ ID No 150 and 151.

Finally, the humanized nucleic acid sequences for 5B9 $V_H$ and 5B9 $V_L$ were agglomerated and amplified by means of overlap PCR using the primers according to SEQ ID No. 152 and 153. The thus generated nucleic acid sequence for the humanized scFv 5B9 ($V_H$-$3\times G_4S$-$V_L$) was cloned humanized via XhoI and ApaI downstream of the humanized scFv CD3 $V_H$-$G_4S$-$V_L$ in the "pSecTag2B_scFv CD3 $V_H$-$G_4S$-$V_L$", whereby the vector "pSecTag2B_scBsTaFv CD3(G4S)-5B9 humanized" was generated.

Cloning of the "scBsTaFv CD3 ($3\times G_4S$)-5B9" Humanized (See Schematic FIG. 1B, at the Middle):

The humanized sequence for scFv 5B9 ($V_H$-$3\times G_4S$-$V_L$) was cloned humanized via XhoI and ApaI downstream of humanized scFv CD3 ($V_H$-$3\times G_4S$-$V_L$) in "pSecTag2B_scFv CD3 $V_H$-$3\times G4S$-$V_L$" whereby the vector "pSecTag2B_scBsTaFv CD3($3\times G_4S$)-5B9 humanized" was generated.

For providing a pharmaceutical composition according to the invention ("modular targeting system 2", schematically shown in FIG. 1C), the following recombinant antibodies were produced:
- recombinant anti-PSCA antibody according to the invention containing a peptide according to SEQ ID No. 76 (herein also referred to as "E7B6"). This antibody is named in the following scFv PSCA(MB1)-E7B6.
- bispecific antibody (scBsTaFv) directed against CD3 and the peptide according to SEQ ID No. 76. The paratope directed against CD3 comprises the following amino acid sequences of the variable regions: heavy chain SEQ ID No. 65, light chain SEQ ID No. 57. The paratope directed against the peptide according to SEQ ID No. 76 comprises the following amino acid sequences of the hypervariable regions of the variable regions: light chain CDR1 SEQ ID No 84. CDR2 SEQ ID No. 85, CDR3 SEQ ID No. 86, heavy chain CDR1 SEQ ID No. 87, CDR2 SEQ ID No. 88, CDR3 SEQ ID No 89. This antibody is named in the following scBsTaFv CD3-7B6.

Cloning of the Humanized scFv PSCA(MB1)-E7B6:

For generating the humanized scFv PSCA(MB1) with E7B6 epitope at the C terminus MB1 [$V_L$-$G_4SG_4SGASAAG_4SG_4S$-MB1 VH]-[$G_4S$-E7B6], shown in FIG. 1C at the bottom), first the agglomeration of the oligonucleotides according to SEQ ID No. 154 and 155 and afterwards cloning of the E7B6 nucleic acid sequence via NotI and XhoI at the 3' end in "pSecTag2B_scFv PSCA(MB1) humanized" ($V_L$-$G_4SG_4SGASAAG_4SG_4S$-$V_H$-$G_4S$, in analogy to the described construct above with the E5B9 peptide) were carried out, whereby the vector "pSecTag2B_scFv PSCA (MB1)-E7B6 humanized" was generated.

Cloning an Effector Module, "scBsTaFv CD3 ($3\times G_4S$)-7B6" Humanized that Binds to T Cells and to the E7B6 Peptide:

For humanization of the variable region of the heavy chain of the 7B6 antibody (specifically directed against the peptide E7B6) overlapping oligonucleotides according to SEQ ID No. 156 to 160 were agglomerated. Afterwards the humanized nucleic acid sequence of the variable region of the heavy chain of the 7B6 antibody (with a $G_4S$ linker peptide, SEQ ID No. 132) was amplified with the aid of the primer pair according to SEQ ID No. 161 and 162. For humanization of the variable region of the light chain of the 7B6 antibody oligonucleotides according to SEQ ID No. 163 to 167 were agglomerated. The humanized nucleic acid sequence of the variable region of the light chain of the 7B6 antibody was amplified with the primer pair according to SEQ ID No. 168 and 169.

Finally, the humanized nucleic acid sequences for 7B6 $V_H$ and 7B6 $V_L$ were agglomerated and amplified by means of overlap PCR using the primers according to SEQ ID No. 170 and 171. The thus generated nucleic acid sequence for humanized scFv 7B6 ($V_H$-$3\times G_4S$-$V_L$) was cloned humanized via XhoI and ApaI downstream of the humanized scFv CD3 $V_H$-$G_4S$-$V_L$ in "pSecTag2B_scFv CD3 $V_H$-$G_4S$-$V_L$", whereby the vector "pSecTag2B_scBsTafv CD3(G4S)-7B6 humanized" was generated.

For the expression of the single fusion proteins of the modular targeting systems 1 and 2, Hek293T cells were transfected with the expression vectors, and the secreted recombinant scFv (scFv PSCA-E5B9 or scFv PSCA-E7B6) and the bispecific antibodies (scBsTaFv CD3 ($G_4S$)-5B9 or scBsTaFv CD3 ($3\times G_4S$)-5B9 and scBsTaFv CD3-7B6) were purified from the cell culture supernatant with the aid of affinity chromatography on Ni-NTA agarose (Qiagen, Hilden, Germany) (if necessary, in combination with a fractionated ammonium sulfate precipitation), By SDS PAGE and Immunoblot the purity and stability of the recombinant antibody derivatives were verified (FIG. 2).

Example 3

Determination of the Dissociation Constant of Binding to PSCA

The determination of the affinity constant for the respective anti-PSCA domain of the recombinant, bispecific antibodies with the anti-PSCA MB1 antibody (according to the invention) and the anti-PSCA 7F5 antibody (comparative example, antibody of [Feldmann 2010]) was based on a flow cytometric analysis of binding to PSCA-positive PC3 cells.

For generating the binding curves of the recombinant anti-PSCA antibody domains, $2\times10^5$ PSCA-positive cells each were incubated with 100 µl of the bispecific antibodies (MB1 and 7F5) for 1 h at 4° C. The antibodies were used in the following concentrations, respectively:

| Antibody amount per batch in ng | Antibody concentration in pmol/l |
|---|---|
| 1,000 | 90,000 |
| 100 | 9,000 |
| 50 | 4,500 |
| 10 | 900 |
| 5 | 450 |
| 1 | 90 |
| 0.5 | 45 |
| 0.1 | 9 |
| 0.05 | 4.5 |
| 0.01 | 0.9 |
| 0.001 | 0.09 |

To verify the specific binding of the recombinant CD3-PSCA antibodies, a mouse-anti-c-myc IgG-FITC assay antibody (AbD Serotec, Düsseldorf, Germany) was used which after completion of the first staining step was incubated for 30 min at 4° C. with the anti-PSC antibody marked PSCA-positive cells. As a negative control, a sample was carried along in which PSCA-positive cells were stained only with the assay antibody mouse-anti-c-myc IgG-FITC. The cells were analyzed in a BD FACS Calibur Flow Cytometer (BD Biosciences Pharmingen, Heidelberg, Germany) and the data were evaluated with the aid of the software WinMDI 2.8 (Joseph Trotter, La Jolla, Calif. USA).

For evaluation, the ascertained MFI values (mean fluorescence intensity values) were plotted against the tested antibody concentrations and in each case a trend line of the polynomic regression type of the second order was calculated. To determine the affinity constant, a trend line was calculated of the polynomic regression type of the second order and was inserted. The binding curve resulting therefrom served as a basis for calculating the affinity constant $K_D$ which is defined as that concentration which is reached at 50% value of the maximum MFI value and therefore is reached at half-maximum saturation of binding. To calculate this constant, the first derivative of the binding curve which follows a square function was formed first. To determine the maximum of the function based on this equation, the first derivative was set to "zero" and solved for x. The maximum of the function $y_{max}$ and therefore $y_{max}/2$ which corresponds to the MFI value at half-maximum saturation of the binding sites was calculated by using the obtained value of x in the source equation. Because the $K_D$ value corresponds to the x value at $y_{max}/2$, it can be finally calculated by employing the $y_{max}/2$ value in the square function of the binding curve and transpose the equation for x.

The following $K_D$ values were determined in this manner for binding to PSCA:

|  | $K_D$ |
|---|---|
| scBsTaFv CD3xPSCA (MB1) | $6.3 \times 10^{-7}$ |
| scBsTaFv CD3xPSCA (7F5) | $2.3 \times 10^{-6}$ |

It was possible to demonstrate in this way that the affinity of the anti-PSCA antibody according to the invention to the antigen PSCA is higher by an order of magnitude in comparison to the antibody 7F5 of the prior art.

Example 4

Specific Lysis of PSCA+ Cells with Bispecific Anti-PSCA Antibodies

In a chrome release test, preactivated PBMCs $5\times10^4$ were co-cultured with $5\times10^3$ $^{51}$Cr-loaded PC3-PSCA tumor cells (effector target ratio=10:1) in presence and absence of the recombinant antibodies in RPMI medium in a total volume of 200 µl. For this purpose, the antibodies according to the invention of example 1 were used (in murine as well as in humanized form). As a comparative example the murine anti-PSCA(7F5) antibody known in the prior art was used in a bispecific antibody of the same configuration. The variable regions of the 7F5 antibody correspond to: heavy chain SEQ ID No. 48 light chain SEQ ID No. 50. Experiments with the following concrete antibody constructs were carried out:

1. humanized bispecific scBsTaFv CD3-PSCA(MB1) from example 1
2. murine bispecific scBsTaFv CD3-PSCA (MB1) from example 1
3. humanized bispecific scBsTaFv CD3-PSCA(7F5) (comparative example)
4. murine bispecific scBsTaFv CD3-PSCA(7F5) (comparative example)

After 20 h incubation at 37° C. in an incubator the chrome released into the medium was measured. The specific lysis was calculated as follows:

Specific lysis in %=[released $^{51}$Cr−spontaneously released $^{51}$Cr(minimum)]/[maximally released $^{51}$Cr(maximum)−minimum]×100%

Figure 3:
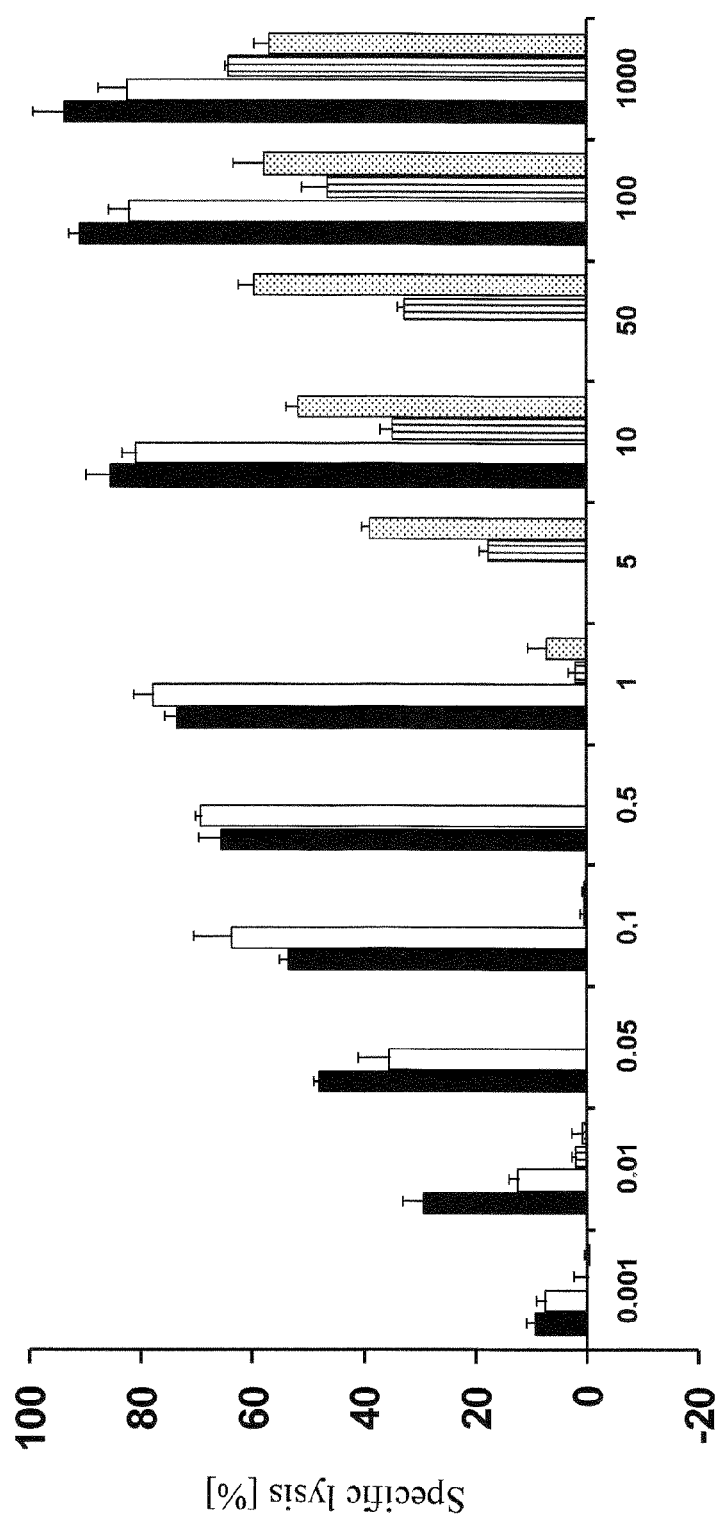
FIG. 3 Specific lysis of $^{51}$Cr-loaded PC3-PSCA tumor cells in the test according to example 4. The bars correspond with the following tests: 1 (black) . . . humanized bispecific scBsTaFv CD3-PSCA(MB1) from example 1; 2 (white) . . . murine bispecific scBsTaFv CD3-PSCA(MB1) from example 1; 3 (striped) . . . humanized bispecific scBsTaFv CD3-PSCA(7F5) (comparative example); 4 (dotted) . . . murine bispecific scBsTaFv CD3-PSCA(7F5) (comparative example).

The results of the in vitro experiment are graphically shown in FIG. 3. The percentage proportion of lysed PC3 cells relative to the total of employed PC3 cells (Y axis) is shown. While the antibodies according to the invention of the experimental groups 1 and 2 already at amounts of less than 1 ng exhibit a strong lysis of the PSCA-positive cells, a detectable lysis can be found with the known 7F5 antibodies in a comparable construct (experimental groups 3 and 4) only upon use of several ng of the antibody. A maximum lysis of about 60% of the employed PC3 cells was determined. With the antibodies according to the invention, a lysis of about 80% of the employed PC3 cells was already observed when using a clearly lower antibody amount. Maximally, more than 90% of the employed PC3 cells were lysed with an antibody according to the invention (experimental group 1).

Example 5

Inhibition of the Tumor Growth by scBsTaFv CD3-PSCA(MB1) Humanized in vivo

As a proof of the efficacy of the anti-PSCA MB1 antibody according to the invention, the effect of a bispecific antibody scBsTaFv CD3-PSCA(MB1) derived from it and produced according to example 1 (schematically shown in FIG. 1A, at the top), was tested in the murine tumor model. As a model organism naked mice were used which form tumors after transfer of PSCA-positive PC3 tumor cells. In the experiment, PSCA-positive tumor cells in combination with T cells and an antibody were transferred.

The following antibodies were used for this purpose wherein per mouse 10 μg of antibody were injected:
(1) bispecific control antibody anti-CD3×anti-5B9 (control)
(2) monospecific humanized scFv anti-PSCA(MB1) from example 1 control)
(3) control without antibody (negative control)
(4) humanized bispecific scBsTaFv CD3-PSCA(MB1) from example 1
(5) humanized bispecific scBsTaFv CD3-PSCA(7F5) as described in example 3 (comparative example)
(6) humanized bispecific scBsDb CD3×PSCA(7F5) which contains the PSCA-binding variable regions of the 7F5 antibody (comparative example)

The effect of the bispecific antibodies is based on the recruitment of the CD3-positive T cells to the PSCA-positive tumor cells and the lysis of the tumor cells mediated thereby.

Figure 4:
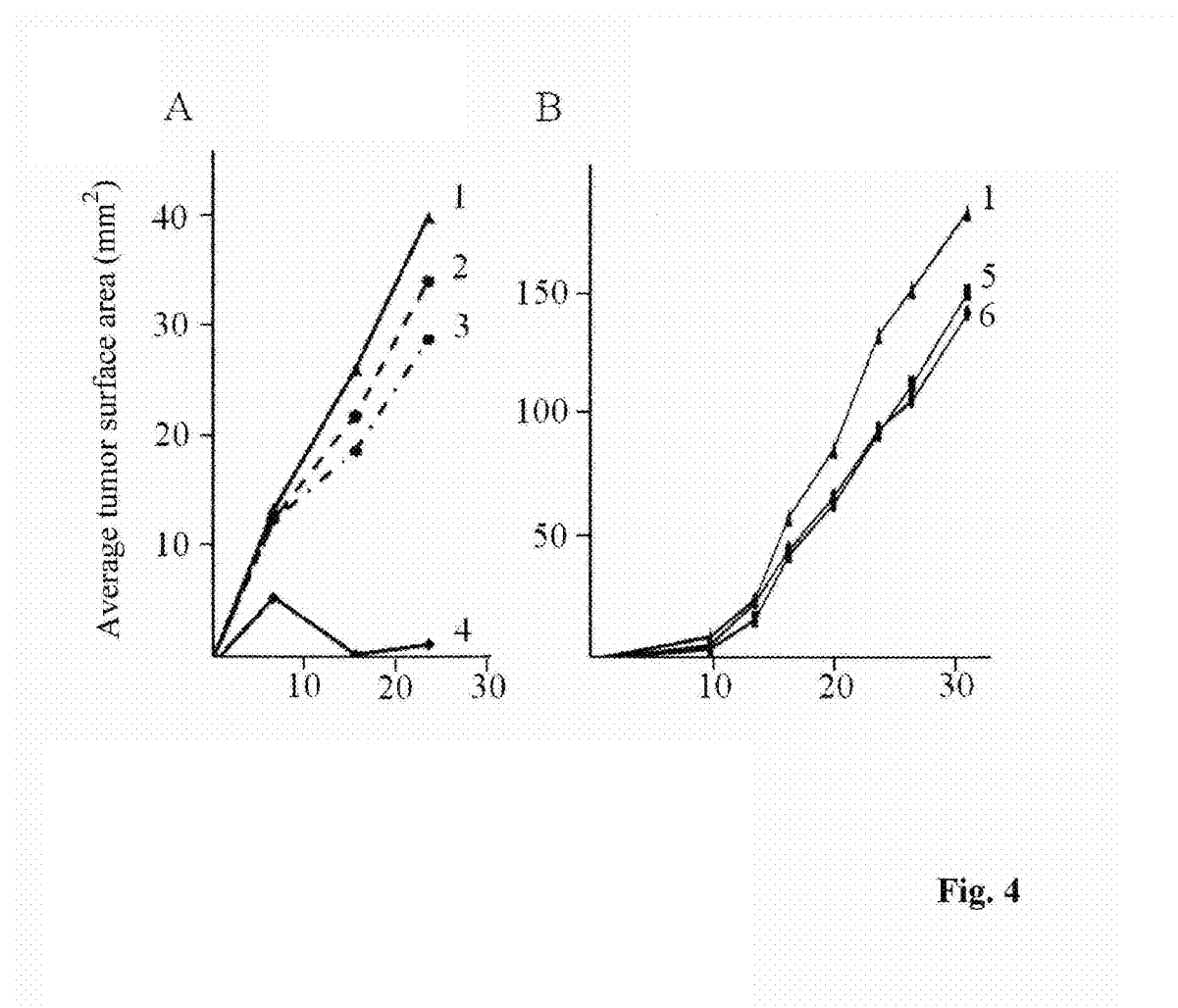
FIG. 4 Formed tumor surface after transfer of PSCA-positive tumor cells, T cells and antibodies, as disclosed in example 5. A) Effector target ratio 1:1; B) Effector target ratio 10:1. The numbered lines correspond with the following tests: 1 . . . bispecific control antibody anti-CD3×anti-5B9 (control); 2 . . . monospecific humanized scFv anti-PSCA (MB1) of example 1 (control); 3 . . . control test without antibody (negative control); 4 . . . humanized bispecific scBsTaFv CD3-PSCA(MB1) of example 1 (according to the invention); 5 . . . humanized bispecific scBsTaFv CD3-PSCA (7F5) as disclosed in example 3 (comparative example); 6 . . . humanized bispecific scBsDb CD3×PSCA(7F5) which contains the PSCA-binding variable regions of the 7F5 antibody (comparative example).

In a first experiment $5\times10^3$ PSCA-positive tumor cells were transferred into 8 naked mice in each experimental group and $5\times10^3$ T cells (effector target ratio 1:1). In the control groups (1) and (3) rapid tumor growth was found in the absence of an anti-PSCA antibody. The control (2) in which monospecific scFv anti-PSCA(MB1) was injected also showed rapid tumor growth. A cytotoxic effect of the monospecific antibody can thereby be excluded and the efficacy can be assigned solely to the bispecific construct. The tumor surface area of the formed tumors was determined 25 days after cell transfer. The three control groups showed no significant difference in the tumor surface area (FIG. 4A).

With transfer of the bispecific comparative antibodies which contain the variable regions of the anti-PSCA 7F5 antibody (comparative groups (5) in the form of a tandem antibody and (6) in the form of a diabody) also a rapid tumor growth was found (data not shown). In a second experiment in which the tumor cells in an effector target ratio of 10:1 (that is with a 10-fold amount of T cells; transfer of $5\times10^3$ PSCA-positive tumor cells and $5\times10^4$ T cells), a rapid tumor growth was also found that showed no statistically significant difference to the control group (1) (FIG. 4B). The tumor growth was not inhibited by the anti-PSCA 7F5 antibodies but was merely delayed somewhat. Even with T cell excess, no in vivo inhibition of the tumor growth by the anti-PSCA 7F5 antibody can be observed.

The transfer of the bispecific antibody scBsTaFv CD3-PSCA(MB1) according to the invention from example 1 with an effector target ratio 1:1 was able to reduce the tumor growth significantly. During 25 days after cell transfer in 2 of the 8 test animal tumors with a clearly reduced surface area (diameter about 2 mm) appeared, 6 of the 8 test animals remained free of tumor (FIG. 4A). The anti-PSCA MB1 antibody according to the invention (experimental group (4)) is therefore clearly superior to the comparably built anti-PSCA 7F5 antibody (experiment group (5)) concerning in vivo efficacy under identical experimental conditions.

CITED NON-PATENT LITERATURE

Feldmann A, Stamova S., Bippes C C, Bartsch H, Wehner R, Schmitz M, Temme A, Cartellieri M, Bachmann M. Retargeting of T cells to prostate stem cell antigenic expressing tumor cells: comparison of different anti-body formats. Prostate. 2011 Jun. 15; 71 (9):998-1011. doi: 10.1002/pros.21315. Epub 2010 Dec. 28.

Gu Z, Yamashiro J, Kono E, Reiter R E Anti-prostate stein cell antigen monoclonal antibody 1G8 induces cell death in vitro and inhibits tumor growth in vivo via a Fc independent mechanism. Cancer Res. 2005 Oct. 15; 65 (20):9495-500.

Morgenroth A, Cartellieri M, Schmitz M, Günes S., Weigle B, Bachmann M, Abken H, Rieber E P, Temme A. Targeting of tumor cells expressing the prostate stem cell antigenic (PSCA) using genetically engineered T-cells. Prostate. 2007 Jul. 1; 67 (10):1121-31.

Reiter, R. E., Gu, Z., Watabe, T., Thomas, G., Szigeti, K., Davis, E., Wahl, M., Nisitani, S., Yamashiro, J., Le Beau, M. M., Loda, M. and Witte, O. N. Prostate stem cell antigen: A cell surface marker overexpressed in prostate cancer. Proc Natl Acad Sci USA. 95(4): 1735-40 (1998)

Roehl, K. A., M. Han, C. G. Ramos, J. A. V. Antenor, and W. J. Catalona. Cancer progression and survival rates following anatomical radical retropubic prostatectomy in 3,478 consecutive patients: long-term results. J Urol, 172 (3): 910-4, September 2004.

Thomas-Kaskel, A. K., R. Zeiser, R. Jochim, C. Robbel, W. Schultze-Seemann, C. F. Waller, and H. Veelken. Vaccination of advanced prostate cancer patients with PSCA and PSA peptide-loaded dendritic cells induces DTH responses that correlate with superior overall survival. Int J Cancer, 119 (10):2428-34, November 2006.

What is claimed is:

1. A prostate-specific stem cell antigen binding antibody, wherein
the complementarity determining regions (CDR) of the variable region of the light chain comprises the following amino acid sequences: CDR1 SEQ ID No. 1, CDR2 SEQ ID No. 2, and CDR3 SEQ ID No. 3, and
the CDR of the variable region of the heavy chain comprises the following amino acid sequences: CDR1 SEQ ID No. 4, CDR2 SEQ ID No. 5, and CDR3 SEQ ID No. 6.

2. The antibody according to claim 1 whose variable regions comprise a humanized amino acid sequence.

3. The antibody according to claim 1, comprising at least two different binding units, wherein
at least one of the binding units binds to prostate-specific stem cell antigen and comprises the complementarity determining regions defined in claim 1, and
at least one other one of the binding units binds specifically to an antigen other than prostate-specific stem cell antigen.

4. The antibody according to claim 3, wherein the at least one other binding unit binds specifically to a surface structure on an effector cell.

5. The antibody according to claim 4, wherein the effector cell is selected from the group consisting of T lymphocytes, NK cells, and monocytes.

6. The antibody according to claim 3, wherein the at least one other binding unit specifically binds to a peptide of a length of 10 to 50 amino acids.

7. The antibody according to claim 3 in the form of a diabody, triabody or tetrabody.

8. A medicament comprising the antibody according to claim 1 for the treatment of tumor diseases.

9. A nucleic acid whose nucleotide sequence encodes for an antibody according to claim 1.

10. A vector containing a nucleotide sequence according to claim 9.

11. An isolated host cell or non-human host organism containing a nucleotide sequence according to claim 9.

12. A pharmaceutical composition containing an antibody according to claim 1 in association with a pharmaceutically acceptable thinner or carrier.

13. A pharmaceutical composition, containing at least two different antibodies in association with a pharmaceutically acceptable thinner or carrier, at least one of said at least two different antibodies being an antibody according to claim 1 and at least one other of said at least two different antibodies being an antibody that specifically binds to said antibody according to claim 1.

14. A diagnostic composition containing an antibody according to claim 1.

15. The antibody according to claim 4, wherein the at least one other binding unit is selected from an antibody or an antigen binding fragment thereof or a ligand binding to a surface structure of the effector cell.

16. The antibody according to claim 6, wherein the peptide of the length of 10 to 50 amino acids is a peptide with an amino acid sequence comprising a partial sequence of the human La protein with a length of 10 to 50 amino acids.

17. The antibody according to claim 6, wherein the peptide of the length of 10 to 50 amino acids is a peptide with one of the amino acid sequences according to SEQ ID No. 75 or SEQ ID No. 76.

18. An isolated host cell or non-human host organism containing a vector according to claim 10.

19. The pharmaceutical composition according to claim 12 in a form suitable for intravenous administration.

* * * * *